United States Patent [19]
Sekiguchi et al.

[11] Patent Number: 5,777,212
[45] Date of Patent: Jul. 7, 1998

[54] SPRING RELAXATION METHOD AND ROTARY VISCOMETER FOR MEASURING RHEOLOGICAL FLOW PROPERTIES OF A LIQUID SAMPLE BY THE METHOD

[75] Inventors: Koji Sekiguchi, Komae; Hattori Sadayoshi, Yokohama, both of Japan

[73] Assignee: Toki Sangyo Co., Ltd., Tokyo, Japan

[21] Appl. No.: 808,103

[22] Filed: Feb. 28, 1997

[30] Foreign Application Priority Data

Mar. 1, 1996 [JP] Japan ................. 8-045106

[51] Int. Cl.$^6$ ........................................ G01N 11/14
[52] U.S. Cl. ............................... 73/54.33; 73/54.35
[58] Field of Search ...................... 73/54.22, 54.32, 73/54.33, 54.35, 54.37

[56] References Cited

U.S. PATENT DOCUMENTS 5,201,214 4/1993 Sekiguchi et al. ............. 73/54.35
5,287,732 2/1994 Sekiguchi ....................... 73/54.33

Primary Examiner—Michael Brock
Attorney, Agent, or Firm—Pennie & Edmonds LLP

[57] ABSTRACT

A rotary viscometer has a control mode for measuring the viscosity of a liquid sample with a high viscosity or a high yield value in an ultra-low shear rate range using a spring relaxation method. In this rotary viscometer, a pivot protecting device attains a locked state in which a pivot is separated from a bearing and a rotor shaft is locked against the rotation therein, a released state in which the lock of the rotor shaft is released while the pivot is in contact with the bearing, and a latched state disposed therebetween, in which the rotation of the rotor shaft is locked and the pivot is in contact with the bearing. Responding to user's instructions, a control device controls a locking motor to bring the pivot protecting device to a designated state, and controls a rotational driving motor in accordance with the state. For the spring relaxation measurement, the control device controls so that the spring is wound up while the pivot protecting device is in the latched state.

9 Claims, 30 Drawing Sheets

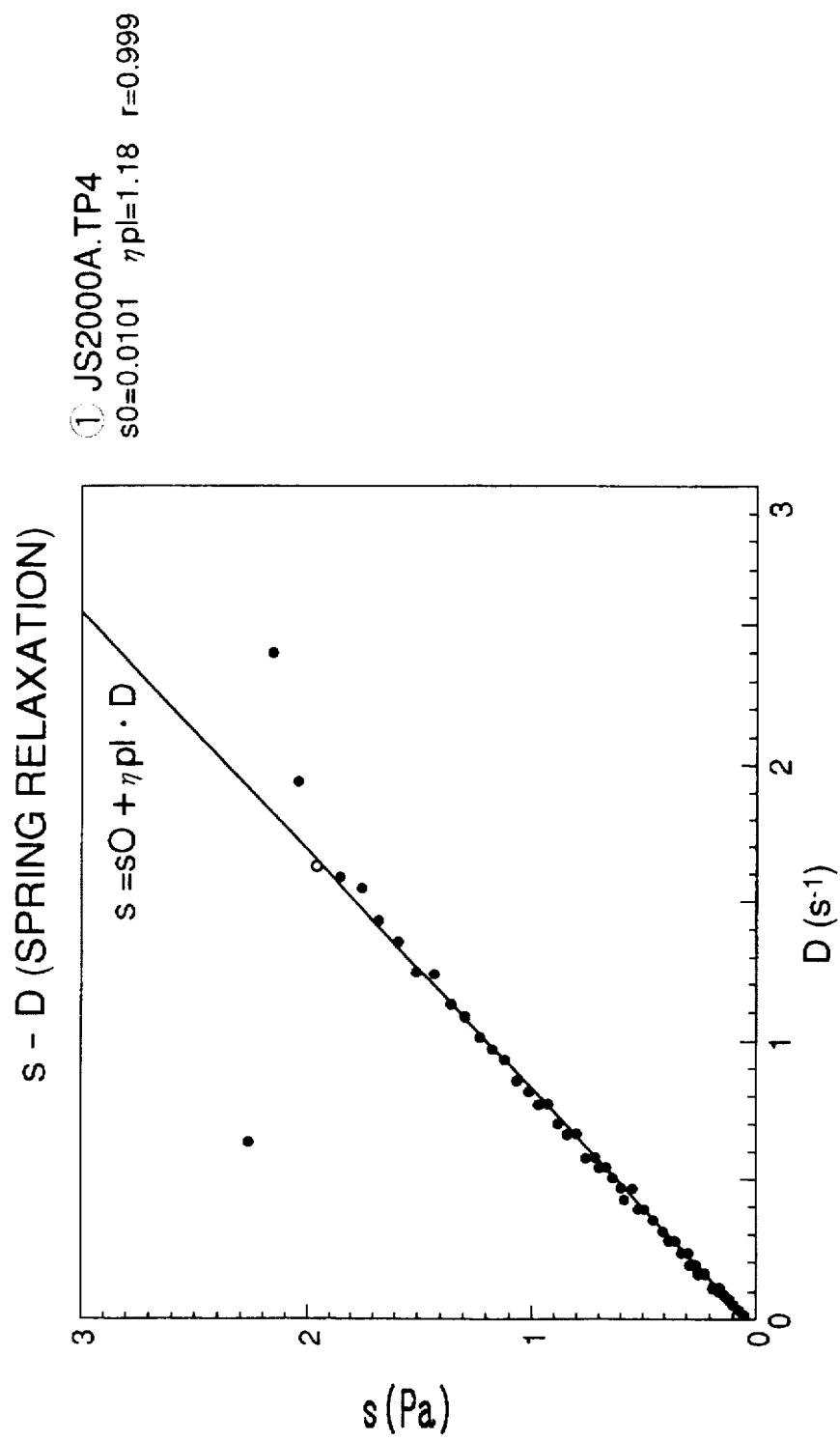

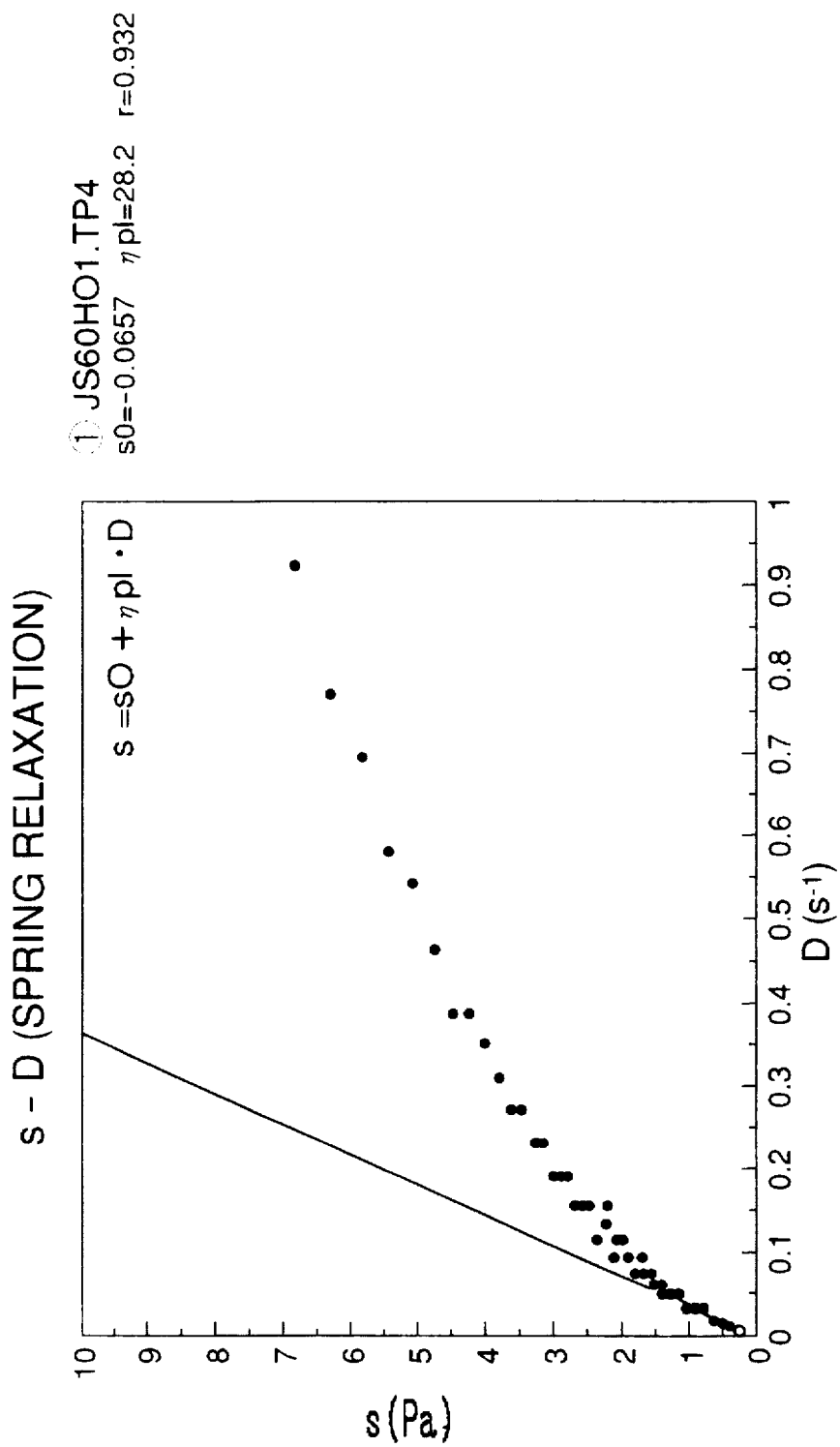

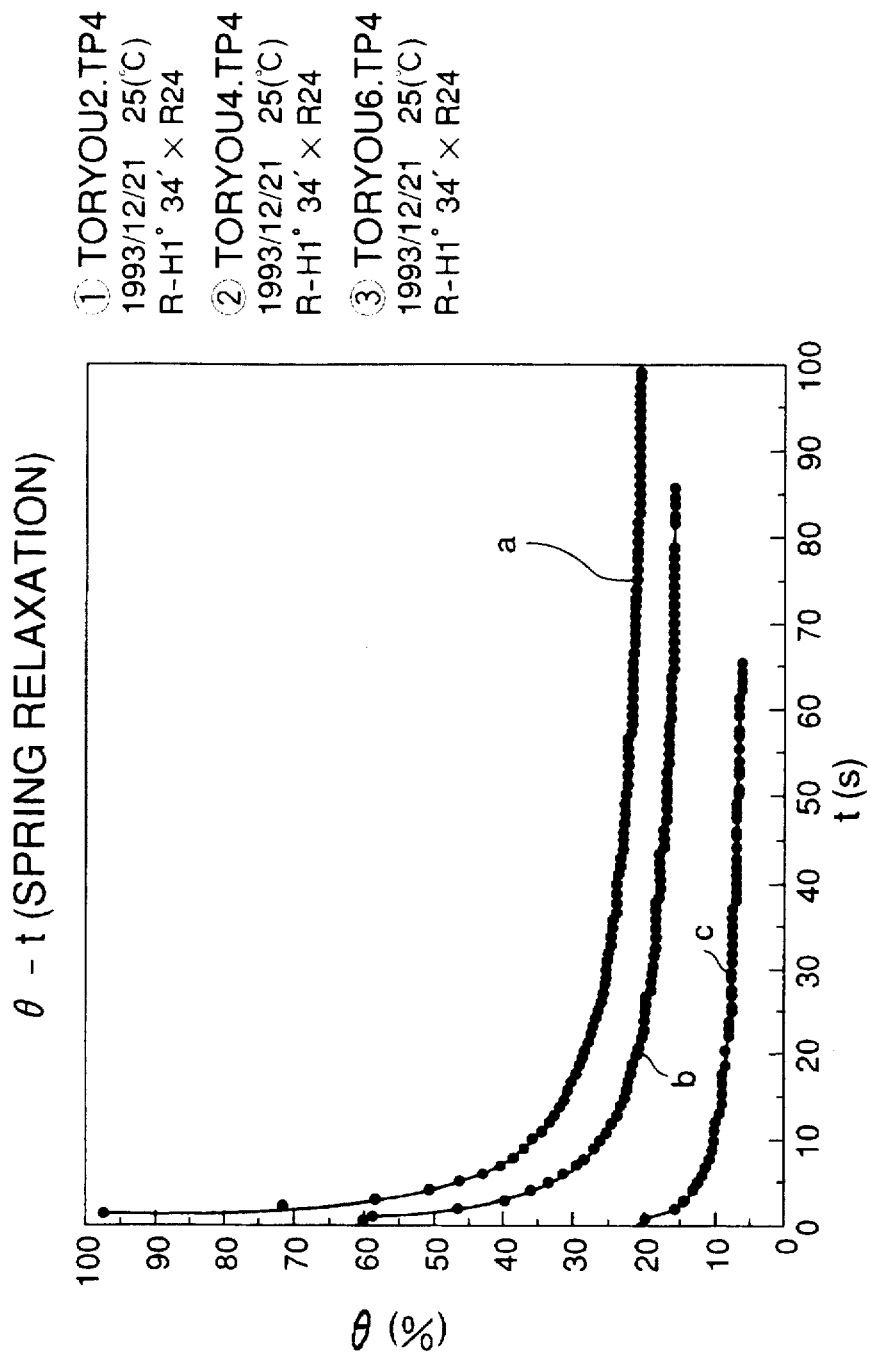

SPRING RELAXATION METHOD AND ROTARY VISCOMETER FOR MEASURING RHEOLOGICAL FLOW PROPERTIES OF A LIQUID SAMPLE BY THE METHOD

BACKGROUND OF THE INVENTION

1. Field of the Invention

The present invention relates to a rotary viscometer for measuring the viscosity of a liquid sample, and more particularly to a spring relaxation method for rheological measurements of the sample liquid in an ultra-low shear rate range and a rotary viscometer which make it possible to conduct such measurements. The spring relaxation measurement is important for checking the quality of coating liquids such as paint or ink used for the coating of solid material surfaces.

2. Description of Related Arts

In most industrial areas which handle liquid materials or products, such as the petrochemical industry, the synthetic chemical industry, the medical industry, the food industry, the paint/ink industry, the semiconductor industry, the paper industry, or the printing industry, the viscosity measurement of the liquid materials or products is conducted to check the quality of those liquid materials or products, or their production processes.

Among various types of viscosity measurement, the spring relaxation method suited for viscous and Theological measurements in the ultra-low shear rate range has been become more popular for checking coating materials such as paint and ink since the quality of the finished surface depends on viscous behavior of the liquid in the ultra-low shear rate range.

In the following, a conventional spring relaxation method is explained using examples of a photo-resist in the semiconductor production process, a paper surface coating material in the paper industry, the paint coating and the screen printing. In these samples, properties and behaviors of liquids are explained, followed by an explanation of how the quality of coating materials depend on viscous and Theological flow properties in the ultra-low shear rate range, and finally the superiority of the spring relaxation, method in measuring those properties is described.

In the case of a coating machine used for coating, while the coating machine is moving, a shear rate, which the coating material to-be-coated would experience during the coating process, is extremely high regardless of the type of machine, namely a knife coater or a roll coater for typical use, and it is as high as approximately $10^3$/sec to $10^4$/sec.

During such a coating process, it is very important to keep the viscosity of the coating material to a proper value suitable for the process condition to continue the stable process and accomplish good quality in the finished surface. The higher the viscosity, the thicker the coating and the lower the quality of the finished surface. In the worst case, the coating may be faded or discontinued since the coating material can't reach all of the applicator of the coating machine. On the other hand, a lower viscosity may speed up the operation since the coating material can be easily fed, but this also causes problems such as a thinner coating and reduced shielding strength of the coating.

In general, the coating material used in this type of coating process is a suspension solvent where a fine powder like pigment is dispersed and suspended in a polymeric solvent. During the measurement of this type of solvent, an amount of change in the rotational speed of the rotary viscometer, i.e. the amount of change in the indicated value of the viscometer with respect to the shear rate change, varies as shown in FIG. 1. There the indicating value does not increase proportionally with the rotational speed. The following model equation with the power law, describing a relationship between shear rate D and shear stress s, is applicable in many cases.

$$s = s_0 + \mu D^n \quad (1)$$

wherein s, $s_0$, $\mu$, D and n denote the shear stress, the yield value, the non-Newtonian viscous coefficient, the shear rate and the viscous shear rate exponent ($1 > n > 0$), respectively.

FIG. 1 shows a relationship between the rotational speed of the viscometer in rpm and the indicated value $\theta$ wherein a water soluble paint for home use was measured and data were sampled at 25° C. The sample was in a thick liquid state without any dilution. Each dot in the figure represents data for a single measurement. FIG. 2. "s-D FLOW GRAPH" showing a relationship between the shear rate D and the shear stress s, can be obtained by multiplying those rotational speed data in rpm by a constant derived based on a rotor cone angle, and by multiplying the indicated value $\theta$ by another constant derived based on a size of the rotor cone and a spring constant of the torque spring of the viscometer.

As mentioned above, the coating material is subject to shear at the shear with an extremely high shearing speed during the coating process while the surface tension and the gravitational force induced at the coated film are the only forces applied on the coated film right after the coating process. In this case, it is desirable for a coating material to have a function to fix defects, such as minute roughness or cuts in the coated film caused by brush marks immediately after the coating process, by using its own surface tension, and to increase the quality of the finished surface of the coating film.

In other words, it is required to keep a low viscosity in which fluidity of the coated film is assured immediately after the coating process. The function to smooth brush marks using the surface tension is called a leveling characteristic. Expressions like "good leveling" or "bad leveling" are also used regarding such a function. A shearing speed inside the coating film when the leveling process takes place is assumed to be in the order of $10^{-1}$ to $10^{-2}$/sec.

On the other hand, the gravitational force acting on the coating film causes some running out of the coating if the viscosity of the coating film is quite low, and then causes a "drip" with a shape of the tear drop. To prevent such "drip", it is desirable for a coating material to have sufficiently high yield value and the viscosity value in the ultra-low shear rate range to be in the order of $10^{-2}$ to $10^{31}$ $^3$/sec.

Further, characteristics of thixotropy may be add to many coating materials. Thixotropy is a phenomenon due to time delay during a recovery period of the internal structure of a liquid, which has been destroyed by shearing.

The structure of the thixotropic coating material which has been destroyed by a process like a spray coating, a knife coating or a brush coating, will be recovered to the original state with time. The recovery time varies from few seconds to several hours depending on the coating material. Also depending on a length of the recovery time, viscous and Theological behavior will be changed.

For printing ink, gelation due to a rapid structural recovery, i.e. an instant viscosity increase, is desirable to clarify printed texts or pictures. On the other hand, for brush coating, it will require time to smooth the brush mark by the leveling process, and rather slow recovery is preferred. At the same time the "drip" may appear if the recovery takes longer than is necessary.

In the above section, major factors which define viscous and Theological behavior of coating materials in the low shear rate range are explained. In the following section, how to measure sizes of such factors and conventional measurement methods to measure those factors will be described.

Normally steady flow fluid analysis is carried out to measure viscous and Theological behavior of liquid. In this analysis, as shown in FIG. 1, a rotational speed of the rotary viscometer is being changed continuously or stepped from a lower value to a higher value, and data of the viscous torque of the rotor is being sampled at various rotational speeds. A value of the shear rate D exerted on a sample liquid can be obtained from the rotational speed of the rotor, and the rotor size, and a value of the shear stress s can be obtained from the viscous torque exerted on the rotor. Therefore numeric values of the non-Newtonian viscous coefficient $\mu$, the viscous shear rate exponent n, and the yield value $s_0$ can be obtained by the regression analysis using the relationship of the equation (1) within the steady flow, range where data is available.

However it is dangerous to judge behavior in the ultra-low shear rate range, which relates to functions important to coating materials as described in the above section, from shear rate data obtained in the steady flow range. This is because the minimum value of the rotation speed is 0.5 rpm for the conventional rotary viscometer, or about 0.1 rpm as shown in FIG. 1 even for a viscometer which is improved in lower rotational speed operation.

Also the shear rates due to such a rotational speed are in the order of about $10^0$/sec, and considered to be still rather large values.

The yield value is defined as a value of the shear stress at the zero shear rate. Therefore the yield value at the zero shear rate may be obtained by extrapolation using data with rather large shear rates obtained in the steady flow range, to determine the Theological flow property such as the yield value. In other words, the yield value is obtained as a analysis value at a point where the equation (1) is expanded. Such a value may include large error, and this analysis method may be considered a somewhat dangerous one.

An expanded figure of FIG. 2 in the vicinity of the zero shear rate D is shown FIG. 3 illustrating a relationship between the shear rate D and the shear stress s. Although the shear stress of about 14 Pa for the minimum shear rate of about 0.4/sec is obtained as shown in FIG. 3, various yield values may be obtained depending on how measurement data are actually connected to extrapolate a value at the vertical axis of the zero shear rate. A curve shown in this figure is obtained by regression analysis of equation (1) with using six data values shown in this figure. It implies that the equation (1) may not hold up to the vicinity of the zero shear rate.

A method with the Casson equation is widely used to obtain the yield value of a coating material like suspension solvent. This method is known as a superior method making it possible to obtain a solution which fits to the actual data better. The method is particularly applicable to a case where a dispersion of a fine solid powder is dispersed in the Newtonian solvent.

The Casson equation is expressed as the following equation.

$$\sqrt{s} = \sqrt{s_c} + \sqrt{\mu_c} \sqrt{D} \qquad (2)$$

wherein $s_c$ is the Casson yield value and $\mu_c$ is the Casson viscosity. The equation (2) shows that $\sqrt{s}$ and $\sqrt{D}$ are in a linear relationship. Therefore a flow curve will be approximately linear as shown in FIG. 4 in which $\sqrt{s}$ and $\sqrt{D}$ are scaled at each respective axis, and square root values of sampled data are plotted therein. The Casson yield value may be calculated by squaring a value of $\sqrt{s_c}$, a crossing point of the $\sqrt{s}$ axis and the extrapolated linear line. This analysis method has an advantage of reducing errors due to individual variations of analysts who conduct the extrapolation analysis since the Casson's fluid curve becomes approximately linear. FIG. 4 is a graph obtained by plotting the Casson curve using data shown in FIG. 1.

However, even if the Casson curve is employed in the analysis, it is still necessary to define a range in which the curve can be regarded as linear in the vicinity of a zero point as shown in FIG. 5 and extend the linear line up to the vertical axis to determine a crossing point when sampled data are not exactly aligned on the linear line like a case of the previous data. So, even if the above mentioned method is used, reliability of the yield value obtained may be low because there is no sampled data near the zero point anyway and one has to use data of a comparably high shear rate range within the steady flow measurement range.

The steady flow measurement method with the rotor being rotated, has reached its applicable limit for such applications described above. To obtain data in the lower shear rate range beyond the limit of the steady flow measurement, there is the spring relaxation measurement method. The principle of the spring relaxation measurement method is now explained.

A basic configuration of a viscometer for conducting the spring relaxation measurement method is shown in FIG. 6. The figure shows a structure of the most simple rotary viscometer which reads out a torsional angle of a spring by an indicating needle disposed on a scale disc while a viscous torque is balanced.

Assuming the cone rotor 6a is rotated manually until the indicating needle 708 points, for example, to 100% of the scale disc 703 and is fixed by using an appropriate method to clamp it down while a driving motor 701 of the viscometer is stopped. In this state, the spring 705 is wound up with an angle corresponding to 100% of the indicated value and a recovery torque is stored therein.

By holding this state, a predetermined amount of a sample liquid 700 is injected between the cone rotor 6a and a base plate 7a. Then, the rotor 6a is unclamped to release the fixed state. The rotor 6a tries to rotate while driven by the recovery torque of the spring 705 wound with receiving a viscous resisting torque. The recovery torque of the spring 705 is gradually decreased as the rotor 6a rotates. Namely the spring 705 relaxes as the rotor 6a rotates. A relationship between the indicated value θ and time t changes like a relaxation curve shown in FIG. 7.

A residual indication θy is approximately related to the yield value, and its existence in the relaxation curve shown in FIG. 7 indicates that the spring 705 can not come back to its original position. A tangential gradient $(d\theta/dt)_P$ at point P of, the relaxation curve in FIG. 7 indicates a rotation speed of the rotor 6a at the point P, i.e. a shear rate $D_P$, and the indicated value $\theta_P$ at the point P indicates a spring torque exerted on the rotor 6a, i.e. a shear stress $s_P$.

Using the tangential gradient $(d\theta/dt)_P$ and the indicated value $\theta_P$ of the point P of the relaxation curve in FIG. 7, the shear rate $D_P$, the shear stress $s_P$, and consequently a viscosity $\eta_a$ can be calculated from the following equations.

$$D_P = \frac{\gamma}{100\alpha} \cdot \left( \frac{d\theta}{dt} \right)_P \qquad (3)$$

-continued $$S_P = \frac{3\theta_F T}{200\pi R^3} \quad (4)$$

$$\eta_a = \frac{s_P}{D_P} \quad (5)$$

wherein α is a cone angle (deg.) of the cone shaped rotor; γ is a torsional angle (deg.) of the spring corresponding to a full scale of the viscometer; T (N·m) is the recovery torque of the spring corresponding to the full scale of the viscometer; R (m) is a radius of the cone rotor; $D_P$ (sec$^{-1}$) is the shear rate; $s_P$ (Pa) is the shear stress; and $\eta_a$ (Pa·s) is the apparent viscosity.

The curve shown in FIG. 7 is obtained with a water soluble paint commercially available for home use, which is the same sample as in FIG. 1, with a measurement temperature of 25° C. This curve represents a common shape of relaxation graph with a yield value. A curve of the relaxation graph showing gradual approach of the indicated value to the zero point can be obtained analytically as in FIG. 8 for Newtonian viscous liquid samples with no yield value. Such samples include, for example, a hydrocarbon standard liquid for calibrating viscometer. The curve can be expressed in the following equation.

$$\theta = K e^{-\beta t/\mu} \quad (6)$$

The relaxation curve shown in FIG. 8 is obtained at measurement temperature of 25° C. for JIS2000, the standard liquid of hydrocarbon oil for calibrating viscometer in accordance with JIS (Japanese Industrial Standards) regulations. K in the equation (6) is an indicated value of the winding angle, and β is another constant determined from the rotor radius R, the cone angle α, the recovery torque T for the full scale angle of the viscometer, and the full scale angle γ of the viscometer.

It would be unrealistic to apply measurement principles of the spring relaxation measurement to a rotary viscometer of the prior art in which indicated values are read out visually using an indicating needle on the scale disc since visual reading and data recording may take too much time.

In other words, a viscometer which make it possible to transform a torsional angle value of the torque spring to an electrical signal, for example, a viscometer with a signal transforming means such as a rotational differential transformer, is required to obtain a series of data like that of the relaxation graph shown in FIG. 7. Further it is also required to A/D convert the transformer's output and store the digital data converted in a computer at a preset time interval, such as one or two seconds. By storing data in the computer, various analysis which suit one's needs may be conducted using the stored data. A basic measurement procedure of the spring relaxation method, like winding up of the spring by manually rotating the rotor, is explained with the example of FIG. 6. Now an improved model of the rotary viscometer of this technical field is suggested by the same inventors of the present invention.

This viscometer will automatically execute all the procedures, including the winding up of the spring. Further explanation regarding this viscometer will be presented later.

The spring relaxation method can obtain continuous data until the rotor comes to a stop or is nearly stopped where the rotor is driven by the recovery torque exerted as the wound-up spring relaxes. In this method, the relationship between the shear rate and shear stress up to the shear rate in the order of 10$^{31}$ $^3$/sec may be used to extrapolate data in the vicinity of the zero point while applying the Casson equation.

Consequently the Casson yield value $s_c$ and the Casson viscosity $\mu_c$ obtained by the extrapolation are much more reliable compared to that of the steady flow measurement.

Examples of the spring relaxation measurement for samples of toothpaste different from the coating material will be explained with reference to FIG. 9 to FIG. 12. FIG. 9 is the spring relaxation graph of this type, and shows a very large residual indication θy. It also shows gradual change in the indicated value after the release of the rotor, indicating that the sample maintains a high viscosity even in a rather high shear rate range which comes immediately after the release.

FIG. 10 is a logs—logD analytic graph showing a relationship between the shear stress s and the shear rate D on a logarithmic scale obtained by a computer operation process using data shown in the relaxation graph of FIG. 9. As shown in the figures, shear rate data obtained by the spring relaxation method reaches a very low shear rate range of 10$^{-2}$ to 10$^{31}$ $^3$/sec.

FIG. 11 is a Casson graph also obtained by computer processing of data shown in FIG. 9. Comparing FIG.11 and FIG. 2, it is obvious that the reliability of the Casson yield value extrapolated by the spring relaxation method is much higher than that of the steady flow method since ample data are available for the shear rate at a range very close to the √s axis in the spring relaxation method.

FIG. 12 is a log$\eta_a$—logD analytic graph which shows a relationship between the apparent viscosity $\eta_a$ and the shear rate D on the logarithmic scale, obtained by computer processing of relaxation measurement data shown in FIG. 9. FIG. 12 can also teach behavior of the apparent viscosity $\eta_a$ with respect to the shear rate in an ultra-low shear rate range.

Various merits in the spring relaxation method for measuring viscous properties in the ultra-low shear rate range, particularly as a method for obtaining the yield value, have been explained while comparing with the conventional steady flow method.

There is a "Rotary Viscosimeter (U.S. Pat. No. 5,287,732)" which carried out the spring relaxation method mentioned above. This invention can be regarded as a prior art relevant to the present invention, and its technical configuration will be explained in the following.

This prior art is based on "Rotary Viscometer Having Pivot Protection Apparatus (U.S. Pat. No. 5,201,214)" to protect the pivot and the jewel bearing of a rotary viscometer, which are fragile and may be easily damaged. This prior art discloses a rotary viscometer which makes it possible not only to perform steady flow viscosity measurements and Theological measurements, but also to carry out the spring relaxation method automatically by adding a function of winding-up of the spring automatically while maintaining the locked state of the rotor shaft.

FIG. 13 shows an example of a structure of the viscometer in accordance with this prior art. Descriptions regarding operations of this viscometer can be found in U.S. Pat. No. 5,287,732.

FIG. 14A and 14B show overviews of the measurement principles for carrying out the spring relaxation method with the viscometer of FIG. 13. FIG.14A shows a state where the viscometer is stopped. In this state, the rotor shaft 5b is locked against rotational movement while the pivot 11 is separated from the jewel bearing 12 and is being protected. A sample liquid is injected between the cone rotor 6a and the base plate 7a while maintaining the previous state. After injecting the sample and entering of the 100% or any other value for the target indicated value θ of the winding angle, the spring relaxation measurement comprising the following steps is automatically started when a start of measurement is instructed.

(1) Starting a pulse motor 21 to rotate while locking the rotor shaft;

(2) Rotating the pulse motor 21 until an output signal from a rotational differential transformer 23 reaches a signal level corresponding to the preset value of the target indicated value θ of the winding angle, and then stopping the rotation to complete the winding up of the spring to the preset indicated value;

(3) After completion of the winding up of the spring, transferring a state of the viscometer to a state for the spring relaxation measurement by recovering a contact between the jewel bearing 12 and the pivot 11 and releasing the lock of the rotor shaft 5b by operating the rotor shaft auto locking device as shown in FIG. 14B;

(4) Conducting the measurement by letting the rotor 6a rotate as driven by the recovering torque of spring 4a wound after releasing of the lock of the rotor shaft 5b, and sending data of the indicated value θ, i.e. spring relaxation measurement data to a computer with sampling interval of one second or two seconds; and (5) Stopping the measurement after elapse of a preset measurement period, and operating the rotor shaft auto locking device to constrain a rotation movement of the rotor shaft 5b and to separate the pivot 11 from the jewel bearing 12, so that the viscometer's state returns to an end state of the measurement in which the pivot is protected.

In this viscometer, a value of γ in the equation (3) is chosen to be 60° since an angle range, in which the linearity can be assured, is selected considering S-shaped conversion characteristic for angles and the electric signal output of the rotational differential transformer 23.

The spring relaxation measurement method has been known as a special measurement method. However, procedures of the method are very complicated and are hardly ever used except for very special cases. Now, a viscometer in accordance with this prior art makes it possible to use the spring relaxation measurement method not only in laboratories but also in fields for check the quality of various materials.

Various samples are measured using the spring relaxation method to study viscous behavior in a low shear rate range using the rotary viscometer of the present prior art. When a high viscous sample or a liquid sample with high yield value is measured, however, peculiar phenomena are observed during the measurement.

First, the peculiarity in the measurement observed on the high viscous sample is explained. In the following, normal measurement results obtained for a low viscous sample are also presented to clarify differences from the high viscous sample.

As an example for the low viscous sample, FIG. 8 shows a spring relaxation graph obtained on JS2000, a standard liquid of hydrocarbon oil for calibrating viscometer. FIG. 15 shows a s-D flow graph indicating a relationship between the shear stress s and the shear rate D both obtained from the spring relaxation graph in FIG. 8. The s-D graph shows that points indicating measurement data are distributed on a straight line which goes through the origin. The result is expected for the standard liquid for calibrating viscometer with the perfect Newtonian viscous flow properties. A viscosity η (=s/D) of 1.18 Pa·s (=1180 mPa·s) obtained from a gradient of the straight line in the graph agreed very well with a value of 1192 mPa·s, the test result data with a measurement temperature of 25° C. obtained for this standard liquid. The test result data of the standard liquid for calibrating viscometer are measured and provided by the National Reserch Laboratory of Metrology of Japan.

As an example for the high viscous sample, FIG. 16 shows a spring relaxation graph obtained on JS60H, a polybutene standard liquid for calibrating viscometer with a measurement temperature of 25° C. FIG. 17 shows a s-D flow graph indicating a relationship between the shear stress s and the shear rate D both obtained from the spring relaxation graph in FIG. 16. Since JS60H is one of standard liquids and has the Newtonian viscous and Theological flow properties, it seems natural to expect that the s-D flow graph obtained on the JS60H standard liquid in FIG. 16 will show the same behavior as the graph of FIG. 15 obtained for JS2000.

However, actual measurement data were not distributed along a straight line which goes through the origin like in FIG. 15, but were distributed on a curved line.

Measurement data in the s-D graph obtained on the standard liquid for calibrating viscometer should be distributed along a straight line which goes through the origin independent of the sample's viscosity. Therefore the measurement data of JS60H distributed along the curved line have to be considered an abnormality.

Next, the peculiarity in the measurement observed on the liquid sample with a high yield value is explained. FIG. 18 shows the spring relaxation graph on a sample liquid of a water soluble paint commercially available for home use without dilution. The graph is obtained for cases where the spring is released after it is wound up to the indicated values of 100%, 60% and 20%. The graph shows that (a) relaxation curve from 100%, (b) relaxation curve from 60% and (c) relaxation curve from 20% have different residual indications from zero. A residual indication from zero corresponds to the yield value as described above, and a single sample liquid cannot have different yield values. Therefore it is abnormal to observe different yield values depending on the indicated value of winding-up angle in the spring relaxation method.

Therefore problems which cannot be neglected seem to be occurring during the measurement when high viscous samples or samples with high yield values are measured using the spring relaxation method of the prior art.

SUMMARY OF THE INVENTION

It is an object of the present invention to provide a spring relaxation method and a rotary viscometer for executing the spring relaxation method which are capable of conducting measurements without experiencing such abnormalities described in the above, even for high viscous samples or high yield value samples, in the same way as the prior art measuring low viscous samples or low yield value samples.

When the spring relaxation measurement is carried out, the sample liquid 700 is injected between the cone rotor 6a and the base plate 7a. It is important for the measurement to fill the whole of a circumferential gap created between the cone rotor 6a and the base plate 7a uniformly with the sample liquid 700 as shown in FIG. 19A, so that the sample liquid 700 is in contact with surfaces of both parts. The measurement will not succeed when the sample liquid 700 is unevenly distributed as shown in FIG. 19B or when there are air bubbles 701 between the gap as shown in FIG. 19C.

It is a further object of the present invention to provide a rotary viscometer which is capable of improving contacts of the sample liquid 700 with surfaces of the cone rotor 6a and the base plate 7a and achieving an ideal arrangement among those parts for measurements in accordance with the spring relaxation method.

Effects of shearing hysteresis on the viscosity or the yield value in a low shear rate range may be studied by using a rotary viscometer for measurements of liquid samples with structural viscous properties. Here the shearing hysteresis has been added on a sample liquid, which is injected between a cone rotor and a base plate, by rotating the cone rotor at a preset rotational speed for a preset time. Effects of the shearing hysteresis can be examined by conducting measurements for various amounts of shearing hysteresis. A structural recovering process of the sample which had been subjected to shearing hysteresis can be also studied by leaving the sample for a certain period of time without rotating the viscometer after adding the shearing hysteresis.

It is a still further object to provide a rotary viscometer which is capable of carrying out measurements for the study of the effects of shearing hysteresis and its structural recovery properties.

In order to accomplish the above mentioned objects, in an aspect of the present invention, there is provided a spring relaxation measurement method with which Theological properties of a liquid sample are measured, comprising the steps of: holding a sample liquid to be measured between a cone shaped rotor which is movable along its rotational axis, and a flat plate which stands still with respect to said rotor; driving said rotor to rotate by a relaxation torque of an elastic member connecting to said rotor while the sample is being held therebetween; and measuring an indicated value of the viscometer while said rotor rotates; wherein said elastic member is tightened up until the indicated value of the viscometer reaches a target value before the measurement starts, and then a constraint of said rotor is released to start the spring relaxation measurement with an assumed peak top of the cone part of said rotor being in contact with said flat plate.

In practical use, a top part of the actual cone shaped rotor is removed as described afterwards. The assumed peak top of the cone rotor here means a position where the top of the rotor is supposed to be before the removal.

In order to accomplish the objects, in another aspect of the present invention, there is provided a rotary viscometer which measures information regarding Theological properties of a liquid sample using a spring relaxation method, comprising; a cone shaped rotor which is supported in such a way that said cone shaped rotor can move along its rotational axis and is driven to rotate while it is in contact with the liquid sample to be measured; rotational driving means having an elastic member connecting to said rotor, for driving said rotor to rotate via said elastic member; locking means for locking rotation of said rotor and releasing the locking condition with having a assumed peak top of the cone part of said cone shaped rotor in contact with a surface of a flat plate which holds the sample liquid between said cone shaped rotor and itself; and control means for controlling a driving operation of said rotational driving means, and the locking and releasing operation of said locking means; wherein said control means has a control mode for measuring a viscosity using the spring relaxation method, and in this control mode executes control operations comprising; locking the rotor rotation by said locking means; tightening said elastic member up to a preset state by operating said rotational driving means; and releasing said locked state of said locking means to change a state of said viscometer to a measurement state for the spring relaxation method.

In order to accomplish the objects, in still another aspect of the present invention, there is provided a rotary viscometer which measures information regarding Theological properties of a liquid sample using a spring relaxation method, comprising; a rotor which is driven to rotate while contacting with a sample liquid to be measured; a rotor shaft which supports said rotor and is a first drive shaft for transmitting a rotational drive force to said rotor; rotational driving means having a drive power source, for driving said rotor to rotate and an output shaft for outputting the drive power; a second drive shaft for transmitting the drive power to said rotor shaft; a first linking means having an elastic member for elastically linking said output shaft with said second drive shaft via said elastic member so as to transmit the drive power therebetween; support means having a pivot and a bearing for rotatably bearing and supporting said rotor shaft; a second linking means which bypasses said support means for linking said rotor shaft with said second drive shaft; indicated value detecting means for detecting an indicated value of said viscometer;

viscosity calculating means for calculating the viscosity from resultant indicated values during a measurement state; pivot protecting means having a locking mechanism for locking and unlocking said rotor shaft against and for rotating, respectively, and a pivot separating mechanism for separating and contacting the pivot of said support means from and with the bearing, respectively; and control means for controlling operations of said rotational driving means and said pivot protecting means, wherein said indicated value detecting means detects rotational angular displacements between said rotor shaft and said second driving shaft, which correspond to said indicated values of said viscometer; said pivot protecting means realizes three states, a first state in which said rotor shaft is locked against rotating and said pivot of said support means is separated from said bearing, a second state in which said pivot of said support means is in contact with said bearing and locking of said rotor shaft is released, and a third state in which said rotor shaft is locked against rotating and said pivot of said support means is in contact with said bearing; and said control means at least has a control mode for measuring the viscosity using the spring relaxation method, in which said elastic member is tighten up to a preset indicated value of said viscometer by operating said rotational driving means and said pivot protecting means is brought into said third state before a measurement starts, and at a start of the measurement said pivot protecting means is further brought into said second state to execute the measurement of the spring relaxation method.

In order to accomplish the objects, in still another aspect of the present invention, there is provided a rotary viscometer which measure information regarding Theological properties of a liquid sample using a spring relaxation method, comprising a cone shaped rotor which is supported in such a way that said cone shaped rotor can move along its rotational axis and is driven to rotate while it contacts with the liquid sample to be measured; rotational driving means having an elastic member, for driving said rotor to rotate via said elastic member; locking means for realizing a second state in which said rotor is rotatably supported while an assumed peak top of the cone of said cone shaped rotor is in contact with a surface of a flat plate which holds the sample liquid with said cone shaped rotor, a first state in which said cone shaped rotor is moved along its rotational axis direction to separate from said flat plate and is locked therein against the rotation, and a third state in which said cone shaped rotor is locked while said assumed peak top of said cone shaped rotor is in contact with said flat plate; indicated value detecting means for detecting an indicated value of said viscometer; and control means for controlling operations of said rotational driving means and said locking means, wherein said control means has a spring relaxation measurement control mode for measuring a viscosity using said spring relaxation method and a preparation control mode for executing a preparation process on the sample liquid before said spring relaxation measurement control mode starts a sequence of operations, and executes operations comprising, in said spring relaxation measurement control mode, tightening said elastic member up to a preset state by operating said rotational driving means and setting said locking means to said third state, and bringing said locking means into said second state to start measurement operations using the spring relaxation method; in said preparation control mode, setting said locking means to said second state, rotating said cone shaped rotor at a preset rotational speed for a preset period of time, stopping said rotor, bringing said locking means into said third state, maintaining the same state in said locking means to leave the sample for a preset period of time which includes a zero value, and changing said control mode to the spring relaxation measurement control mode after an elapse of said preset period.

BRIEF DESCRIPTION OF DRAWINGS

FIG. 15 is an s-D graph obtained for JS2000 standard liquid using the spring relaxation measurement.

FIG. 17 is a s-D graph obtained for JS60H standard liquid using the spring relaxation measurement.

FIG. 18 is a graph showing three relaxation curves obtained for thick water soluble paint using the conventional relaxation measurement method where each of the curves corresponds to a different indicated value of winding angle.

DESCRIPTION OF THE PREFERRED EMBODIMENTS

Before explaining the preferred embodiments of the present invention, causes of the abnormalities mentioned in the "DESCRIPTION OF RELATED ARTS" section as the problems to be solved by the present invention will be described in detail.

As mentioned above, one of the abnormalities was observed during the measurements of Newtonian liquid samples with high viscosity values as having data in the s-D flow graph, which are distributed not along a straight line which goes through the graph origin but on a curved line. Another abnormality was observed for high yield value samples as having different residual indications in the indicated value of the viscometer for different relaxation curves, each of which was obtained for different target values of winding angle, and making it impossible to determine a single yield value for each sample. Although these two abnormalities in measurements seems to be different phenomena, the inventors of the present invention have discovered that there was a common cause for these abnormalities.

Specifically, the abnormalities were found to be caused by an elevating operation of the rotor shaft which simultaneously occurred with the locking operation during the conventional spring relaxation measurement method wherein it is necessary to lock the rotor shaft by operating the rotor shaft auto locking device for pivot protection in order to wind up the spring.

Figure 1:
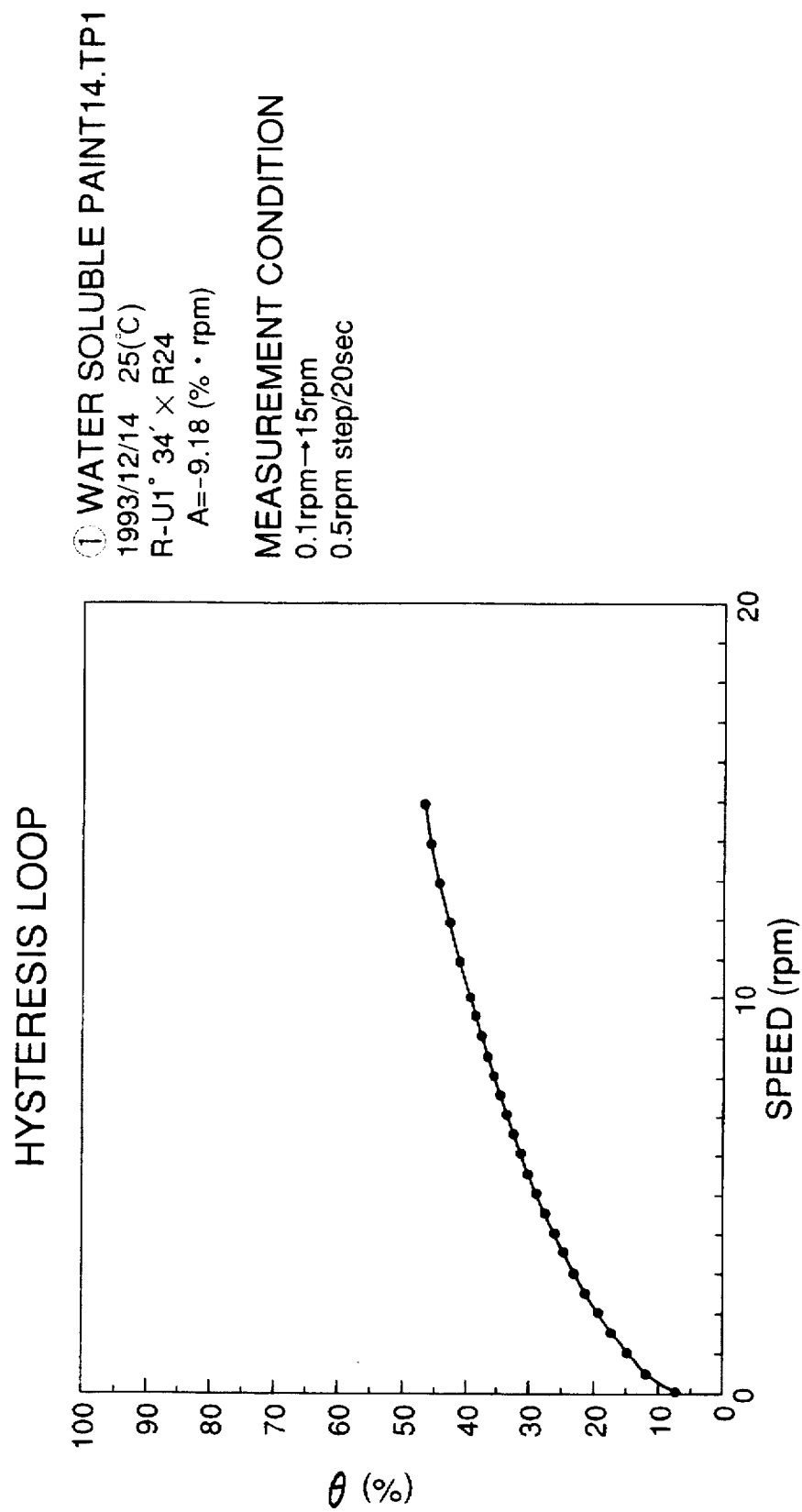
FIG. 1 is a graph showing a relationship between a rotational speed of the rotor and the indicated value obtained by the conventional rotary viscometer.
Figure 2:
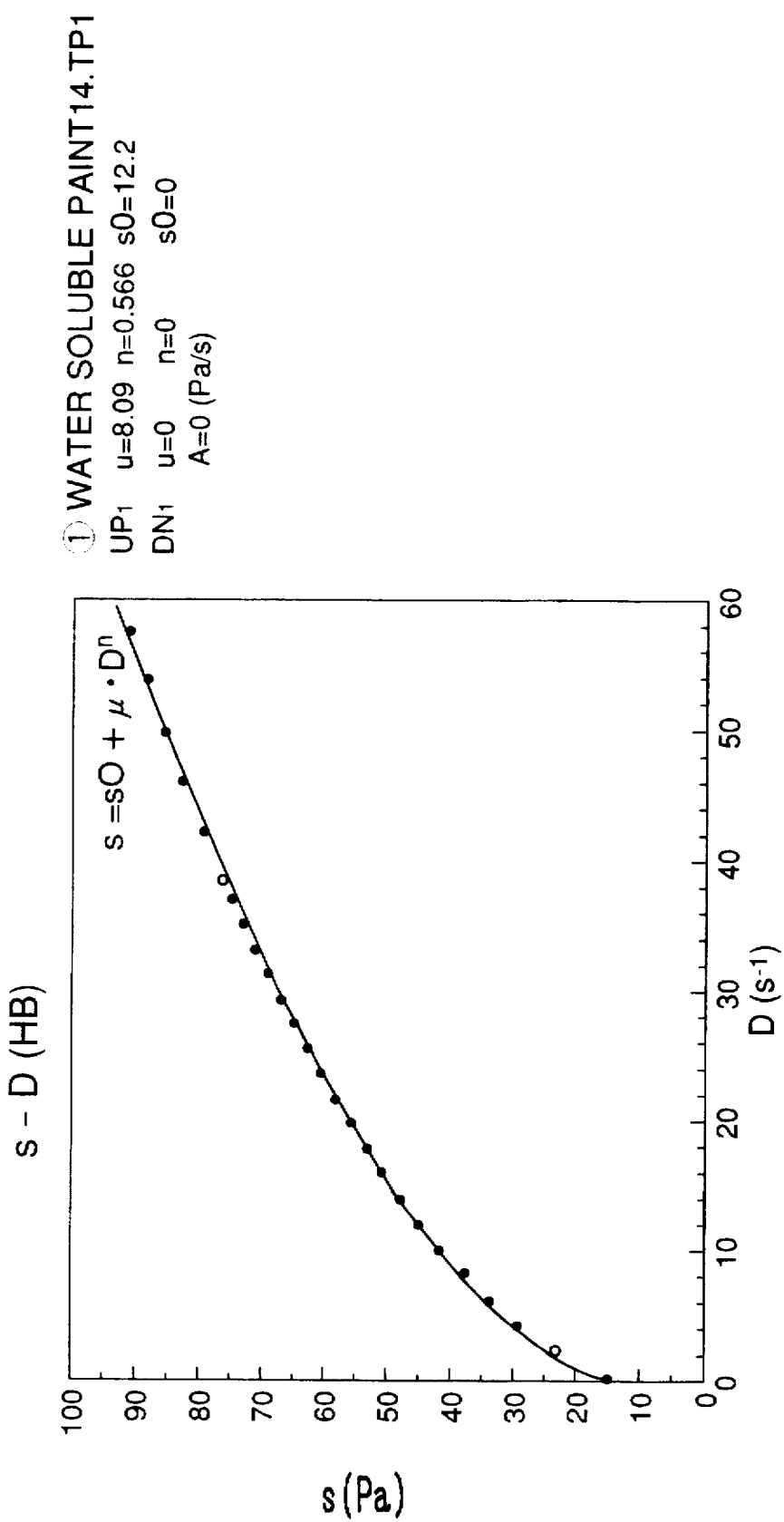
FIG. 2 is a flow graph showing a relationship between the shear rate D and the shear stress s obtained from FIG. 1 data.
Figure 3:
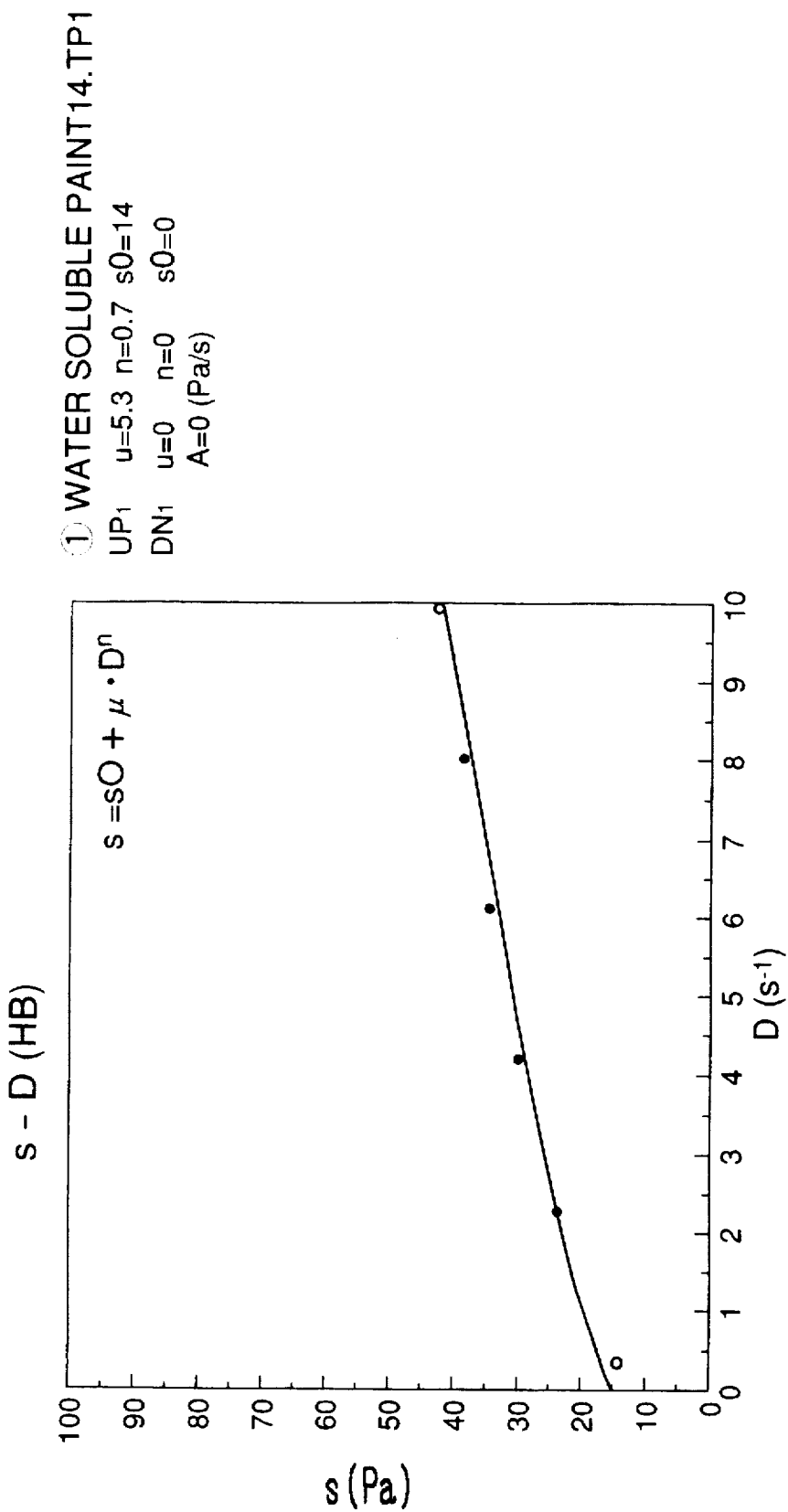
FIG. 3 is a flow graph showing a relationship between the shear rate D and the shear stress s in the vicinity of zero shear rate point (D=0) with an enlarged scale for FIG. 2 data.
Figure 4:
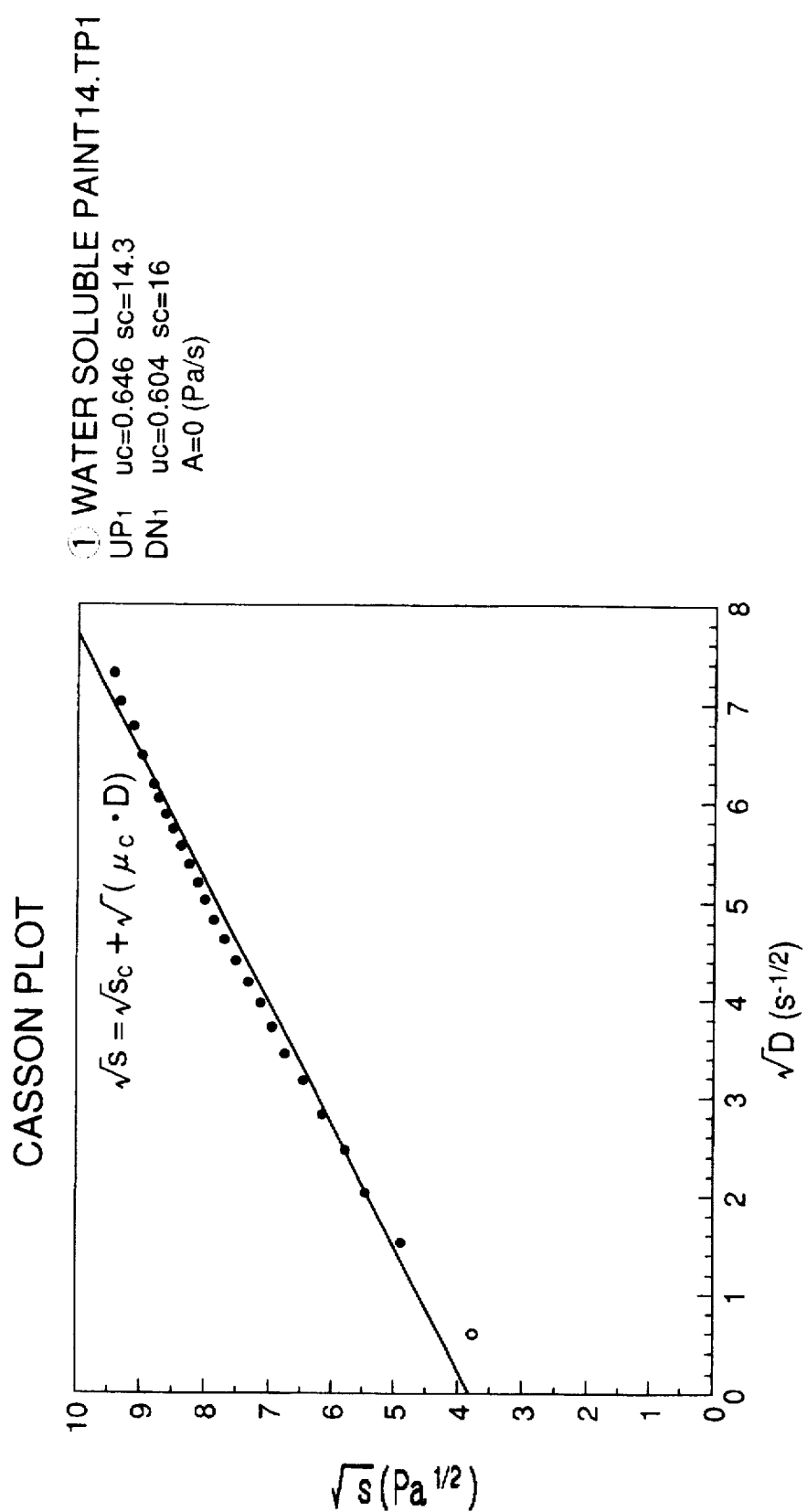
FIG. 4 is a graph showing a Casson curve obtained from FIG. 1 data.
Figure 5:
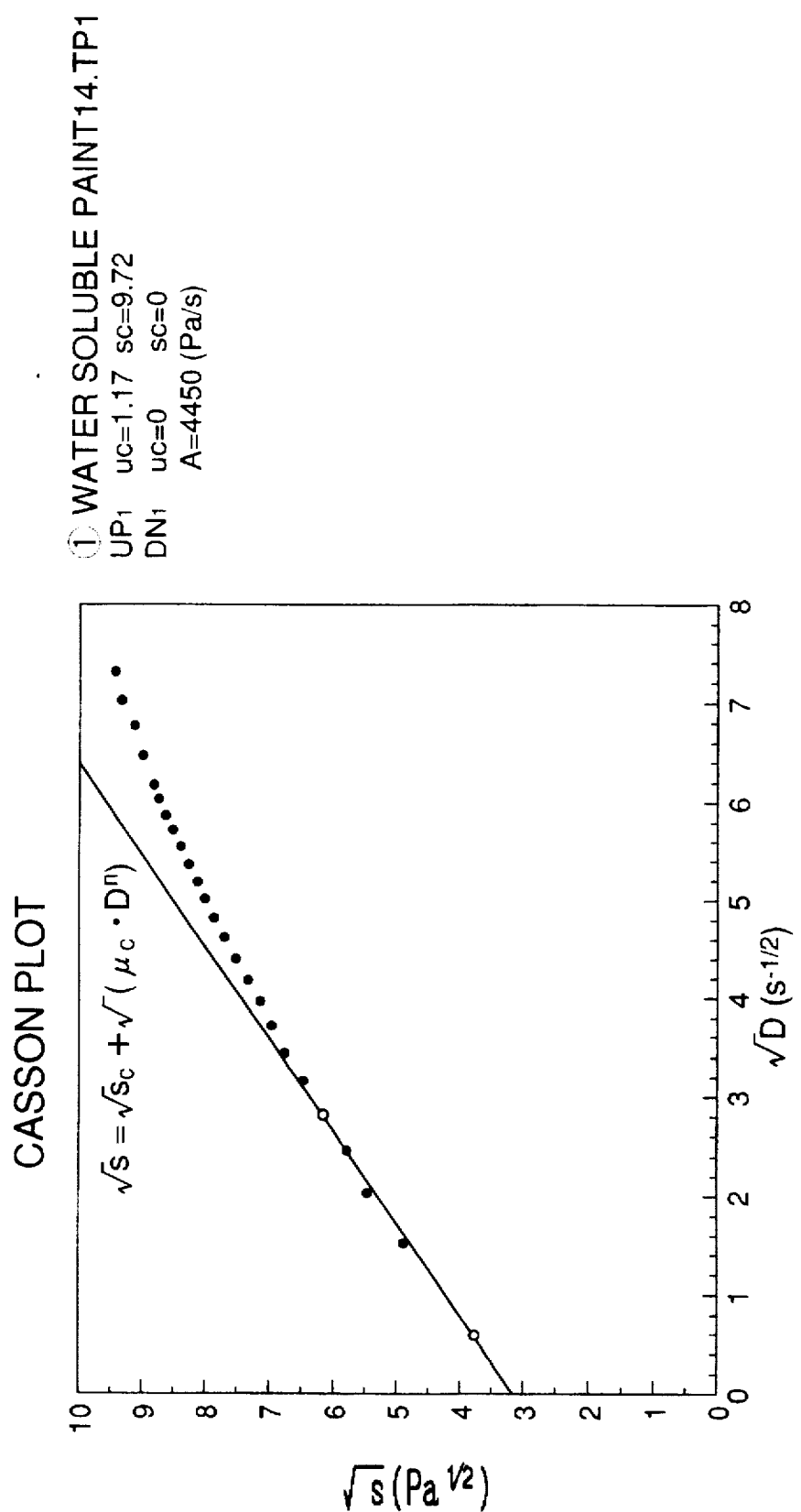
FIG. 5 is a graph showing a Casson curve obtained from FIG. 1 data.
Figure 6:
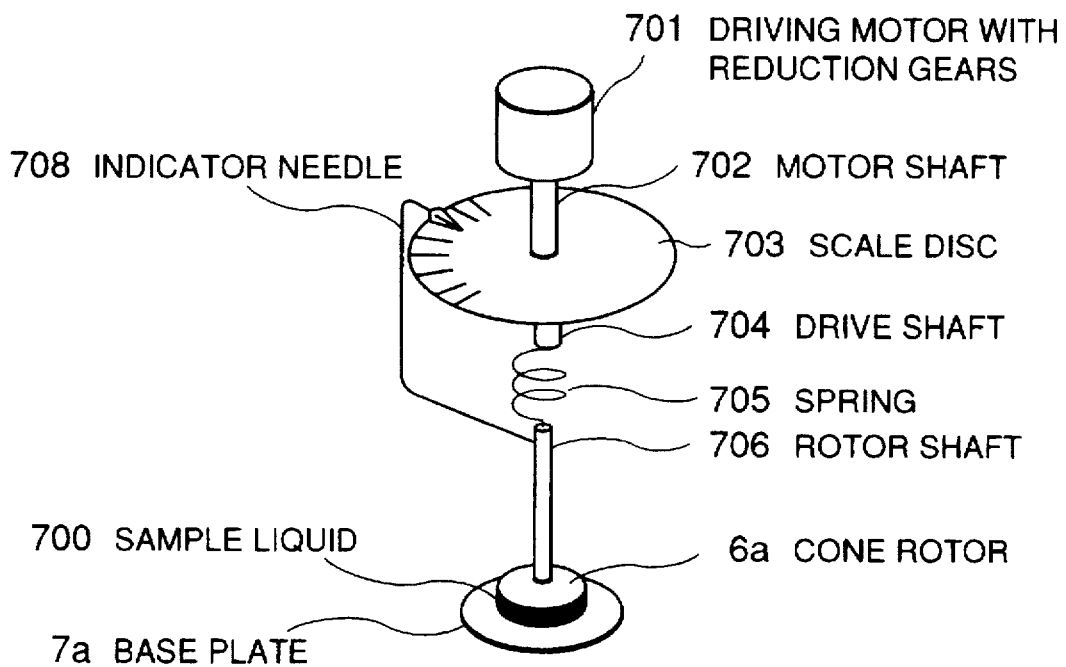
FIG. 6 is an explanatory view of the prior art to explain measurement principles of the conventional spring relaxation method.
Figure 7:
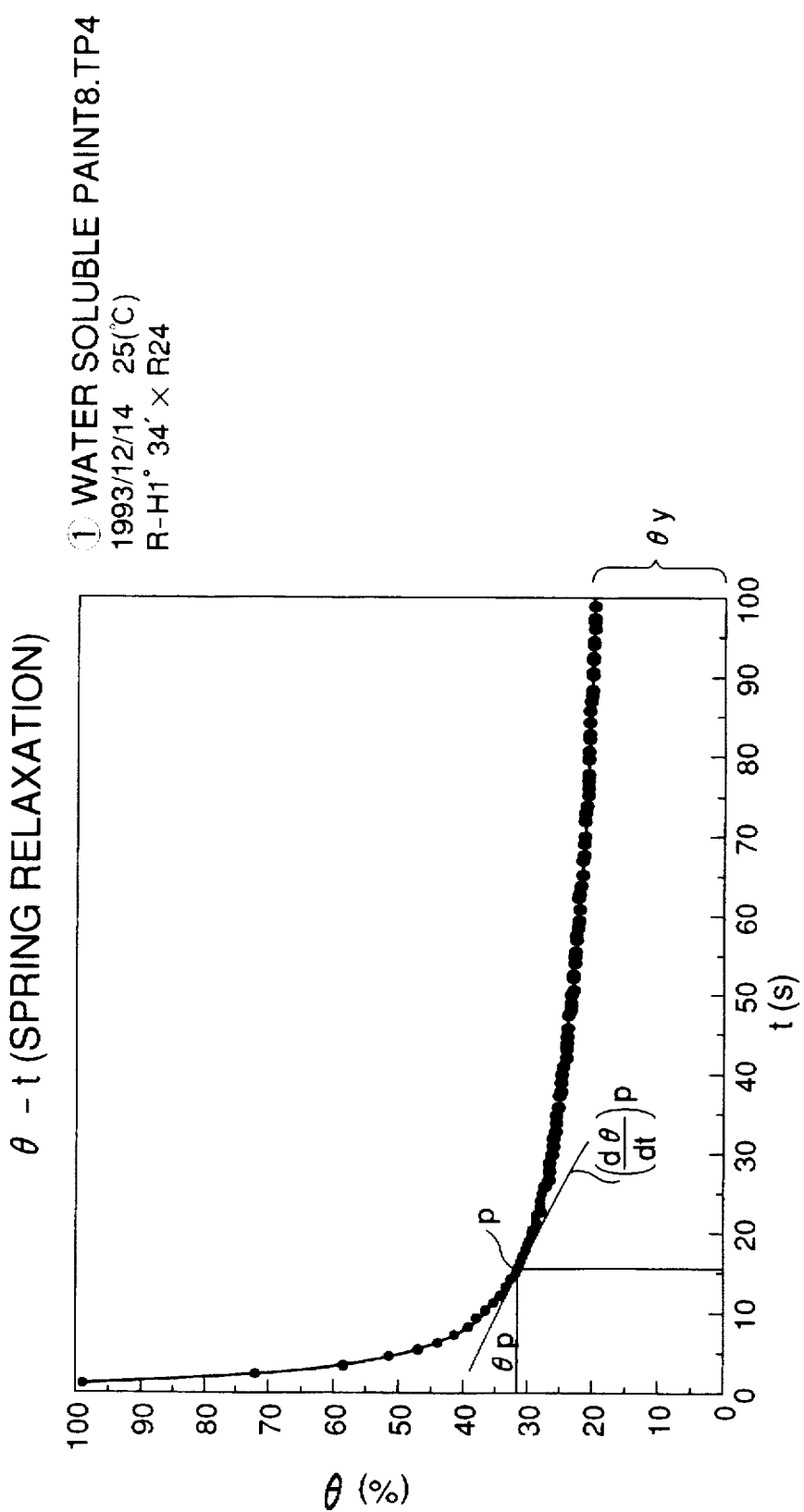
FIG. 7 is a graph showing a relaxation curve obtained by the conventional spring relaxation method shown in FIG. 6.
Figure 8:
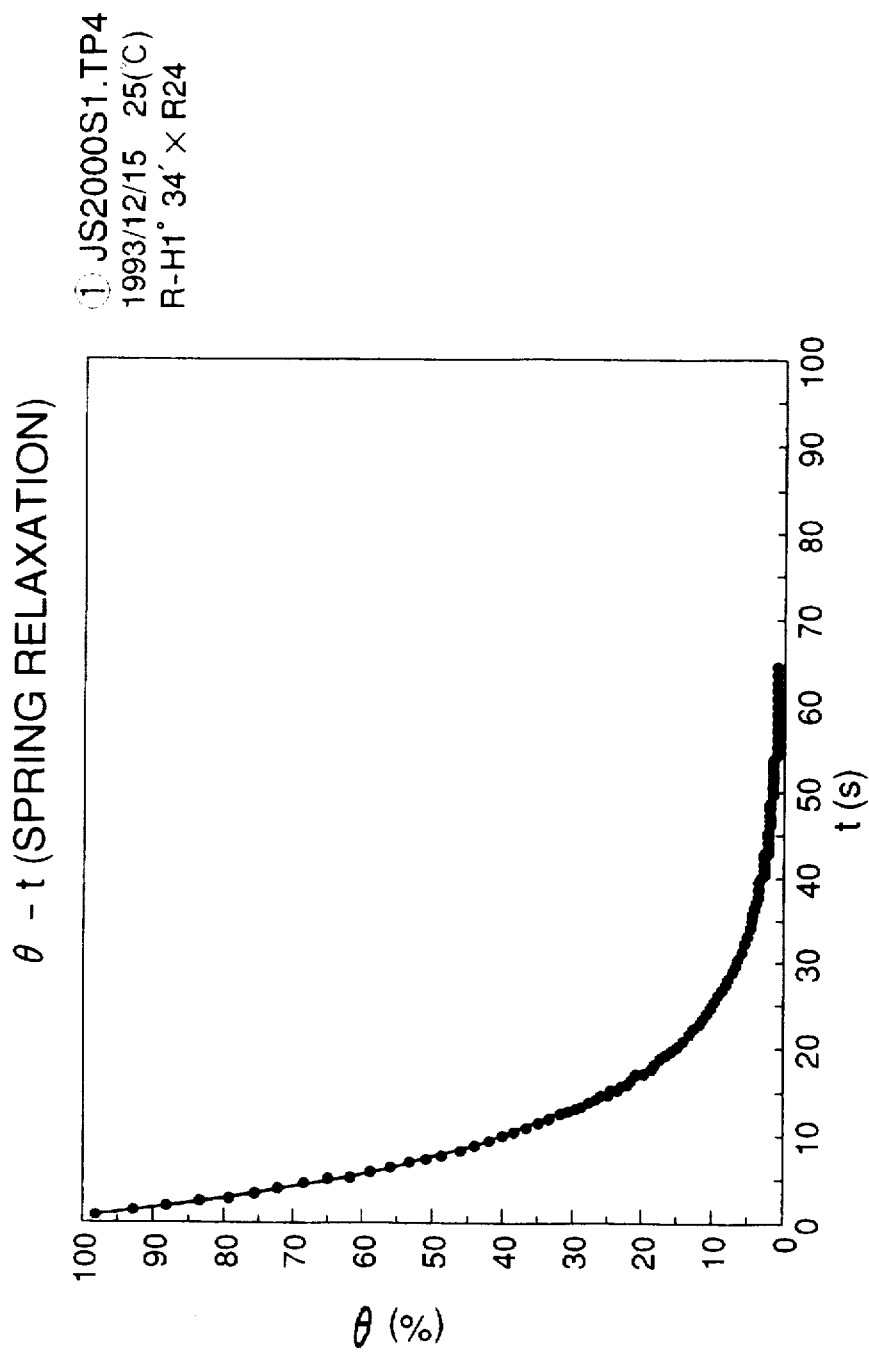
FIG. 8 is a graph showing a relaxation curve obtained by the conventional spring relaxation method shown in FIG. 6.
Figure 9:
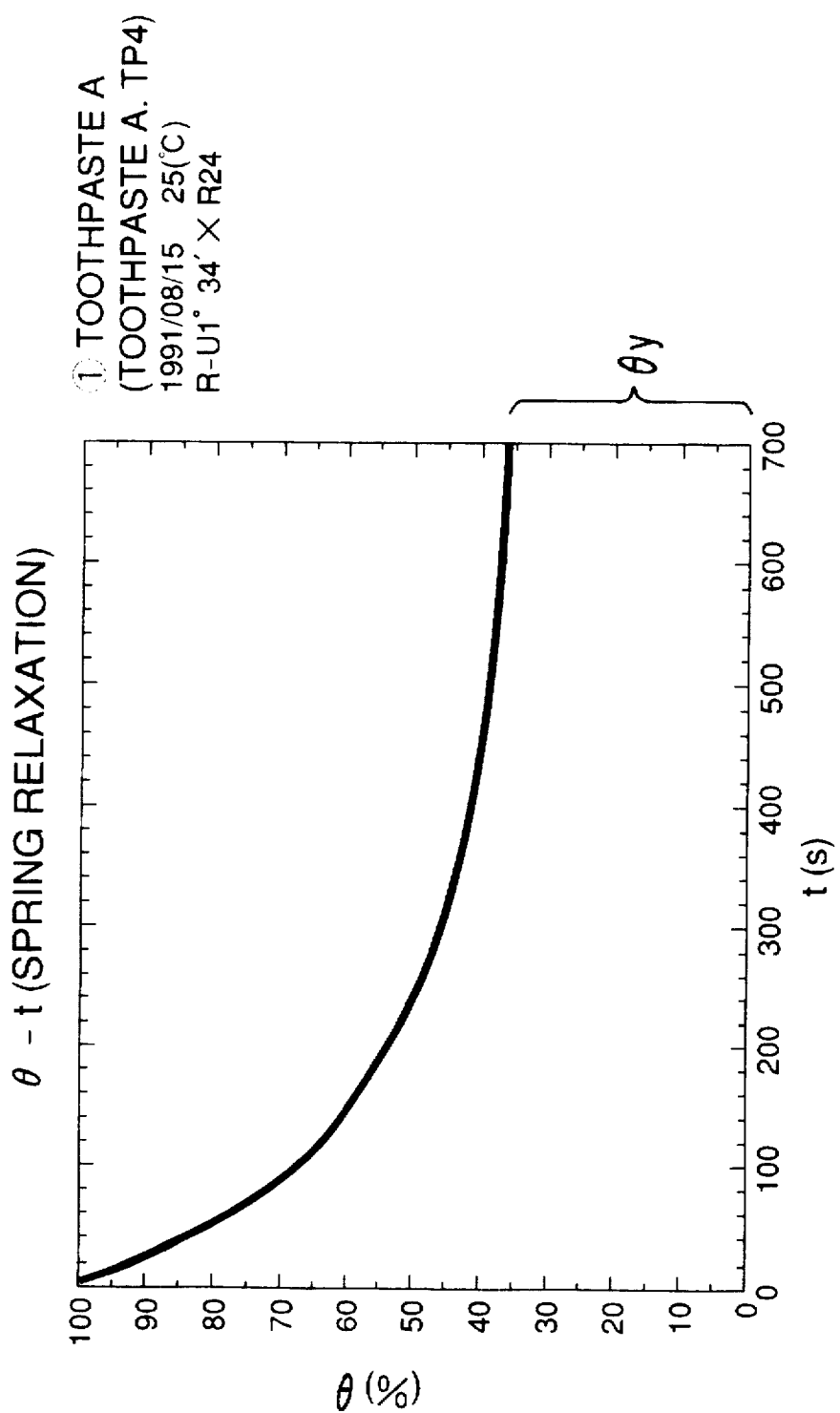
FIG. 9 is a graph showing a relaxation curve obtained for toothpaste by the conventional spring relaxation method.
Figure 10:
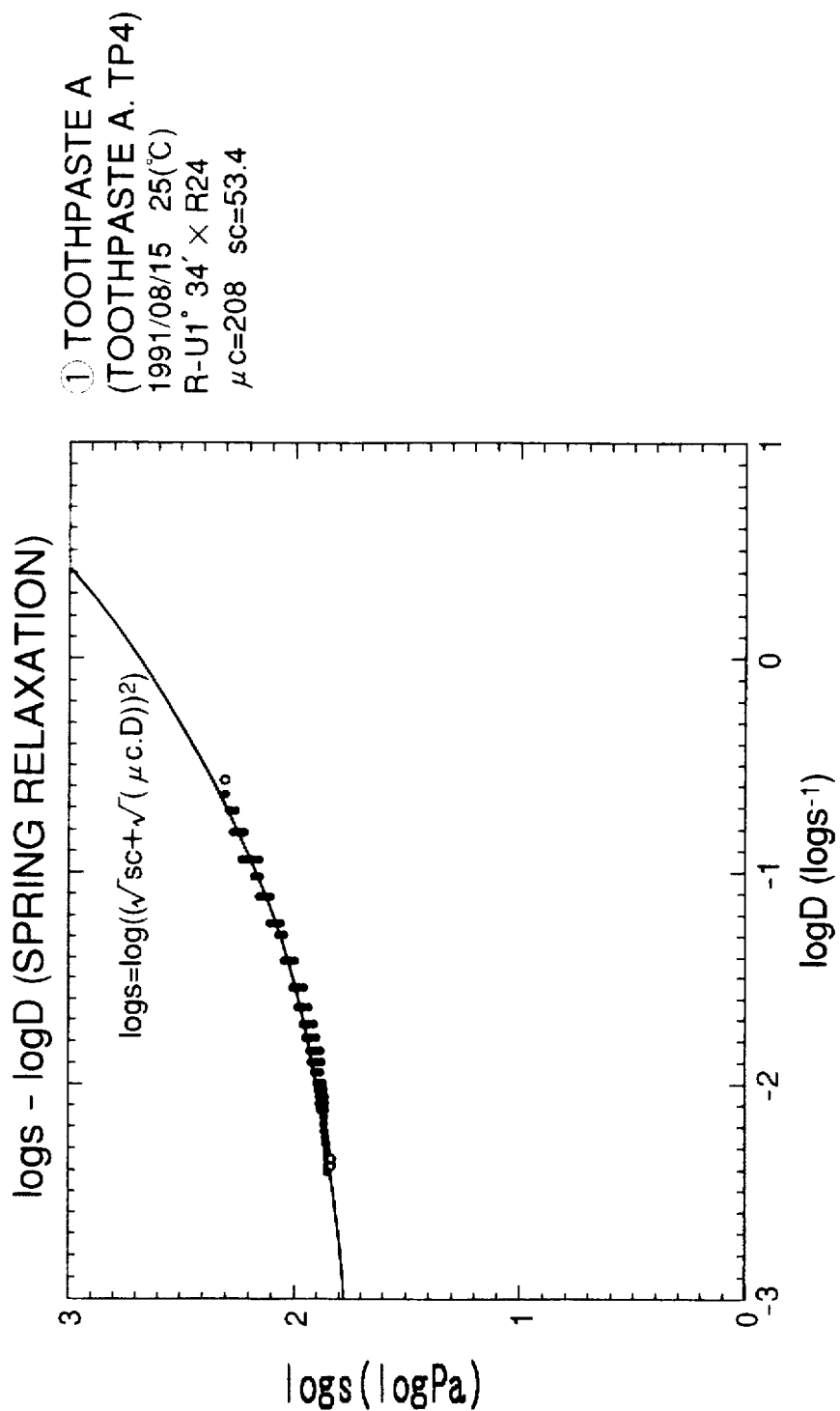
FIG. 10 is a logarithmic scale graph showing a relationship between the shear rate and the shear stress obtained for FIG. 9 data.
Figure 11:
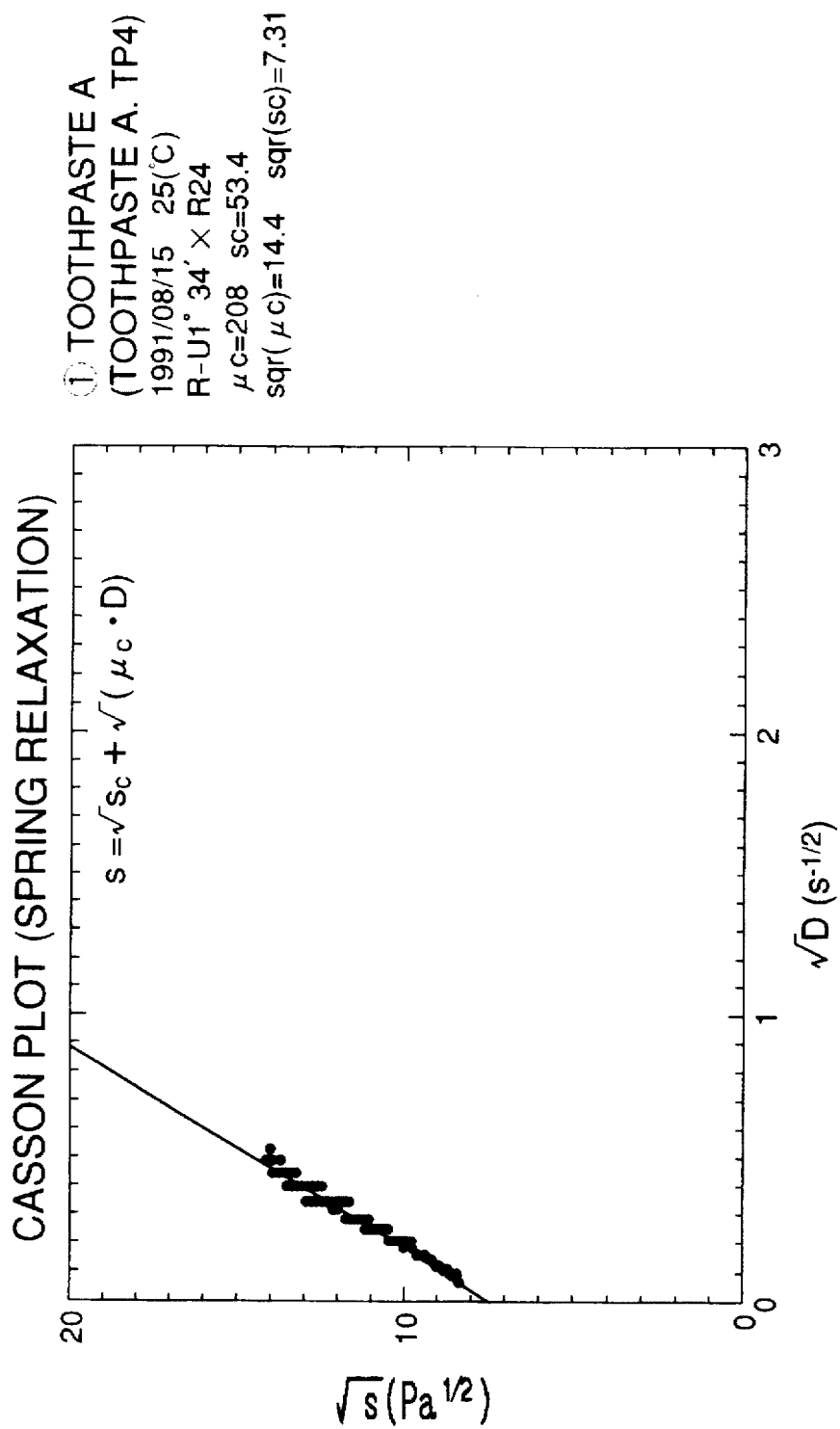
FIG. 11 is a graph showing a Casson curve obtained for FIG. 9 data.
Figure 12:
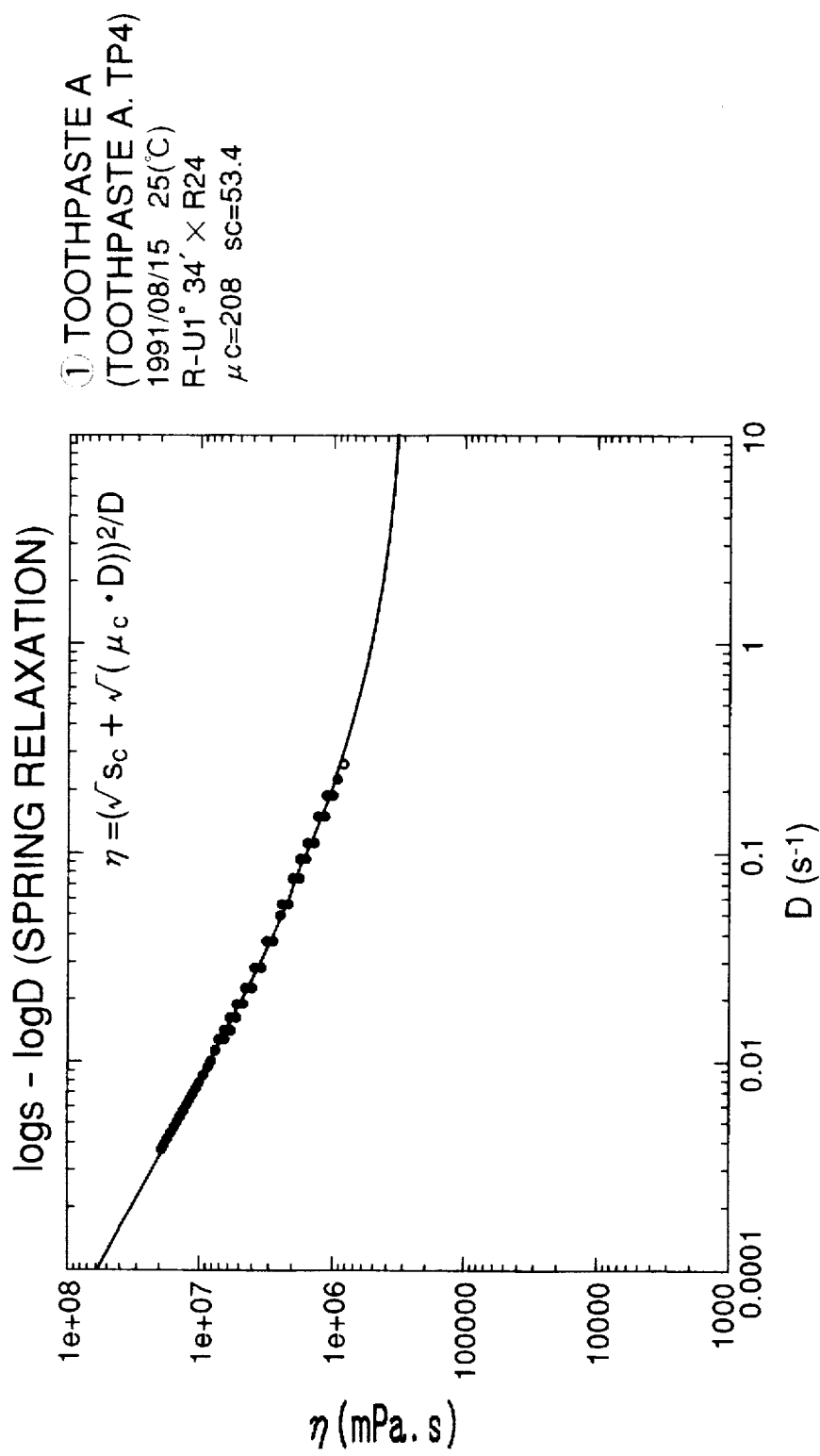
FIG. 12 is a logarithmic scale graph showing a relationship between the apparent viscosity and the shear rate obtained for FIG. 9 data.
Figure 13:
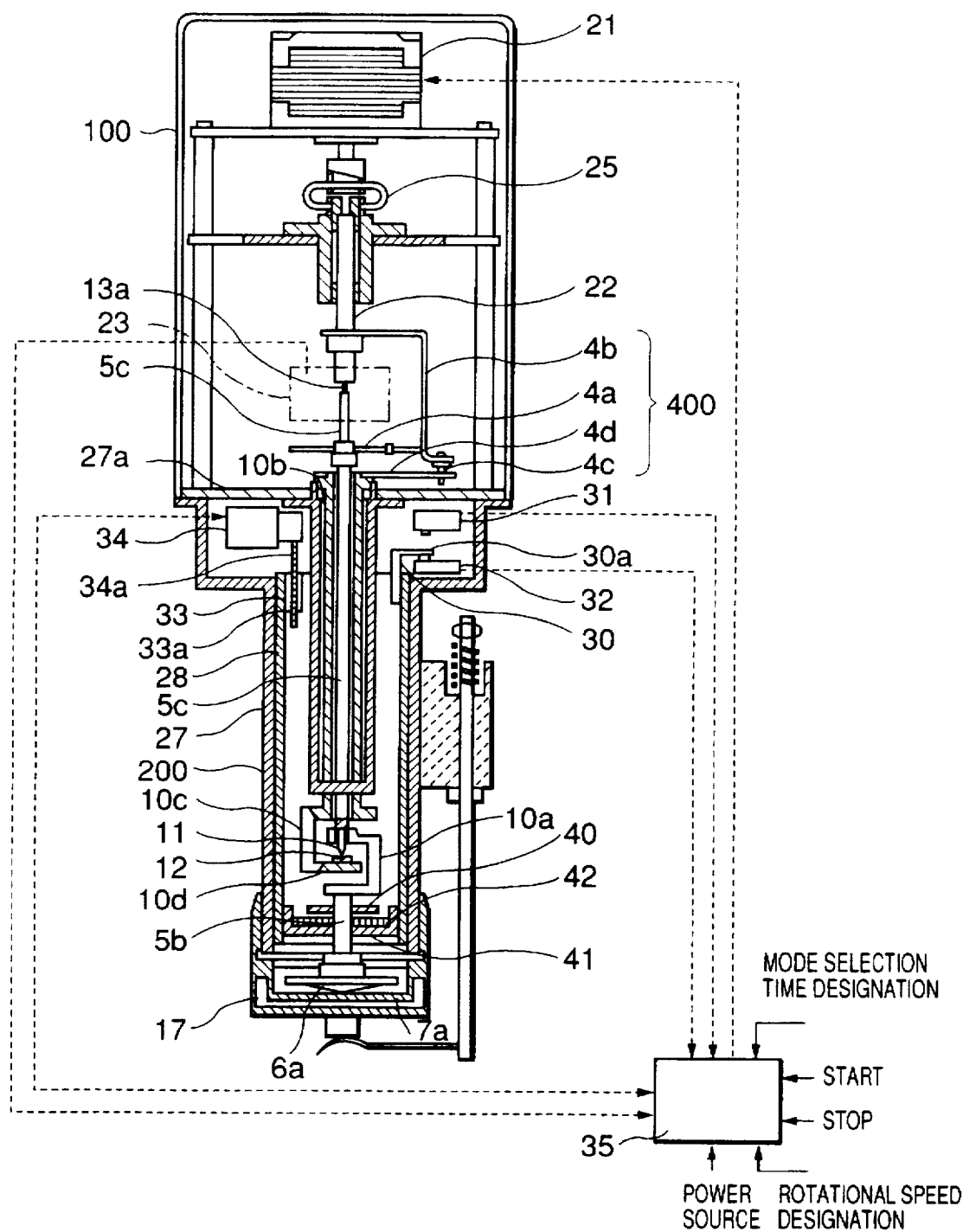
FIG. 13 is a sectional view showing the structure of a rotary viscometer which conducts the spring relaxation measurement of the prior art.
Figure 14A:
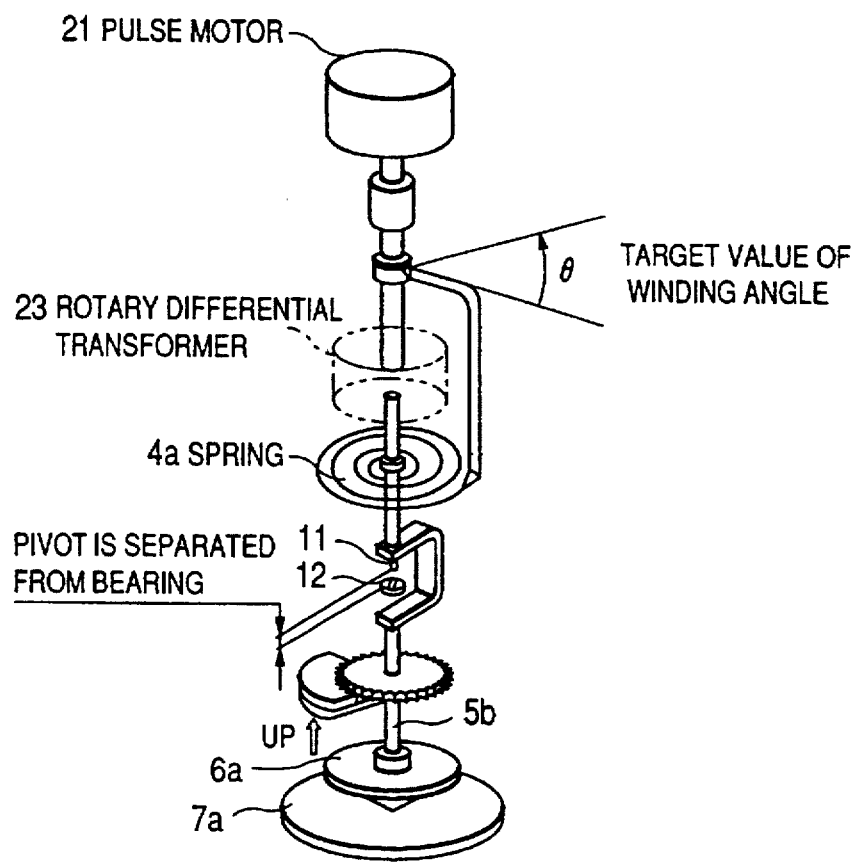
FIG. 14A is an explanatory view of the rotary viscometer shown in FIG. 13 in a state where the pivot and the bearing are separated and the rotor shaft is locked.
Figure 14B:
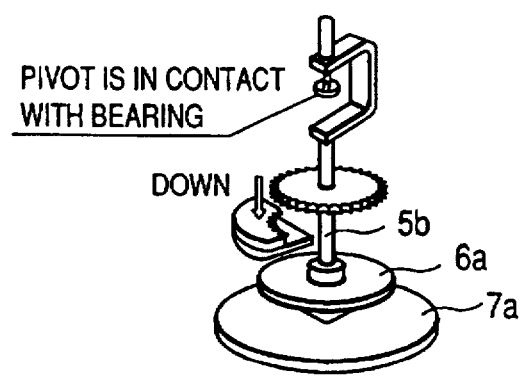
FIG. 14B is an explanatory view of the rotary viscometer shown in FIG. 13 in a state where the pivot and the bearing are in contact and the rotor shaft is released.
Figure 16:
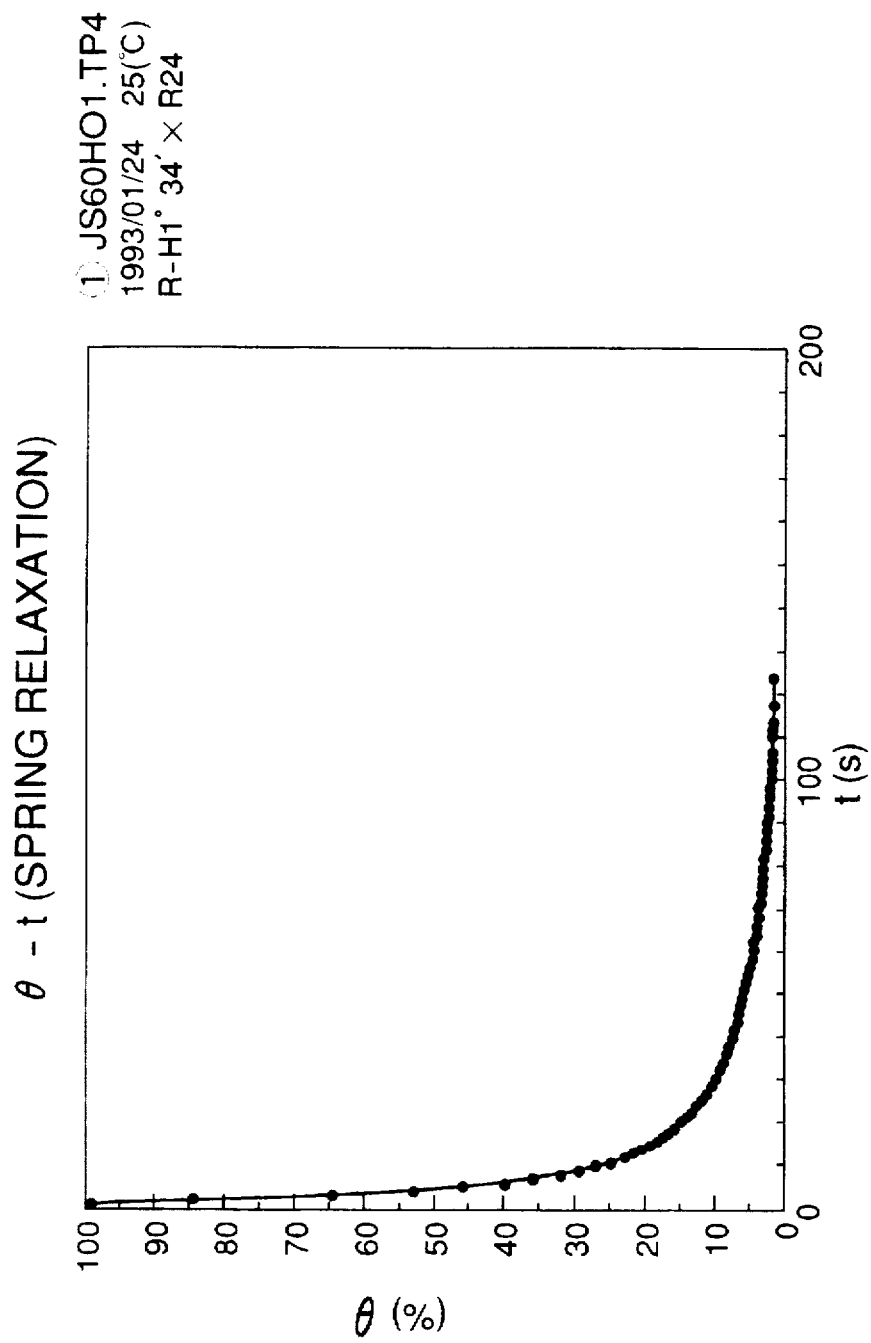
FIG. 16 is a spring relaxation graph obtained for JS60H standard sample using the spring relaxation measurement.
Figure 19A:
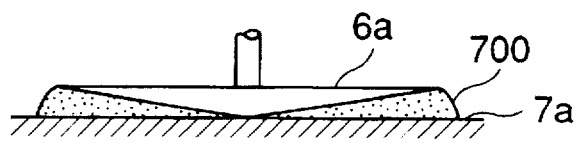
FIG. 19A is an explanatory view showing a relationship among the rotor, the base plate and the sample liquid.
Figure 19B:
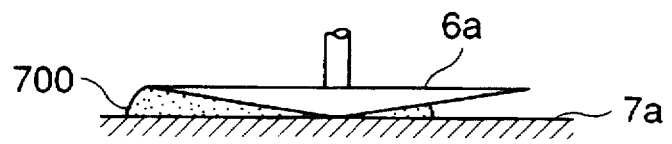
FIG. 19B is an explanatory view showing a relationship among the rotor, the base plate and the sample liquid.
Figure 19C:
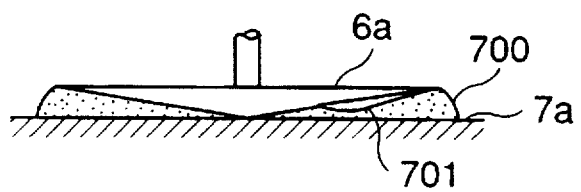
FIG. 19C is an explanatory view showing a relationship among the rotor, the base plate and the sample liquid.
Figure 20A:
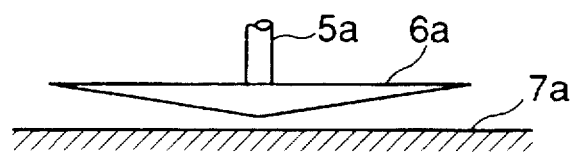
FIG. 20A is an explanatory view showing a relationship between the rotor and the base plate when the rotor is elevated.

As shown in FIG. 20A, when the rotor shaft 5b is elevated, the cone rotor 6a connected to the rotor shaft 5b is separated from the base plate 7a. There the sample liquid 700 between the cone rotor 6a and the base plate 7a is absorbed and flows toward the center of the rotor as the cone rotor 6a becomes elevated higher as shown in FIG. 20B, and eventually it takes on a bridge-like shape bridging the rotor 6a and the base plate 7a.

Figure 20B:
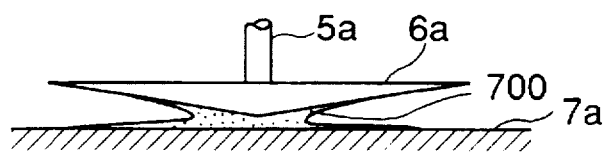
FIG. 20B is an explanatory view showing a relationship among the rotor, the base plate and the sample liquid when the rotor is elevated.

When start of the spring relaxation measurement is instructed, as shown in FIG. 20B the spring is wound up by rotation of the pulse motor to 100% or any other designated value of the indicated value of the viscometer while the rotor shaft is in the locked state. After completing the winding up operation, the rotor shaft auto-locking device starts its operation to reverse the elevation of the rotor shaft 5b and to release the locking of the rotation. Then data measurements are started, and measured data are sent to an information processing device such as a personal computer.

Although the elevating operation of the rotor shaft 5b is released, the sample liquid 700 will not start to flow immediately after the release since the viscosity of the sample liquid 700 is high. Therefore as shown in FIG. 20B the rotor 6a remains on the top of the sample liquid 700, and is unable to make uniform contact with the sample liquid 700 over the whole area of the cone shaped rotor surface which is supposed to be in contact with the sample liquid.

If the locking of the rotor shaft 5b is released and the recovery torque of the spring starts to be exerted in the above-mentioned condition, a viscous torque, like the one which may be generated during the measurement having an ideal state of contact, would not be generated. The viscous torque generated in this case is less than that of the ideal state of contact. Therefore the rotor 6a starts to rotate like in a case where no load is applied because resisting loads against the rotor rotation are loads only due to the partial viscous torque mentioned above and a moment of inertia of a torque detecting shaft system including the rotor 6a.

In addition to the rotation of the rotor 6a mentioned above, the rotor 6a starts to move down as the sample liquid 700 starts to flow and the rotor 6a sinks therein since a downward force due to the weight of the torque detecting shaft system, including the rotor 6a, is applied upon the sample liquid 700. As a result, the area of contact with the sample liquid 700 in the rotor 6a increases, and a value of the viscous torque approaches the normal value for the ideal condition for the spring relaxation method.

In this case, values of the shear rate, which are measured immediately after the start of the measurement by the spring relaxation method, are higher than that of the ideal measurement condition. This abnormal state with higher shear rate is corrected with elapsed time. However, data measured in a period with the abnormal state, which indicate abnormally higher shear rate value, are sent to a personal computer, with time information as the relaxation measurement data.

To test this hypothesis, the elevation function of the rotor shaft auto-locking device is disabled, and only the rotor shaft locking function is made available. With this configuration the pivot protection function will be lost. As the high viscous liquid sample, three types of polybutene standard liquids for calibrating viscometer, JS15H, JS60H, JS200H are measured by a viscometer in which the elevation function of the rotor shaft auto-locking device is disabled.

Figure 21A:
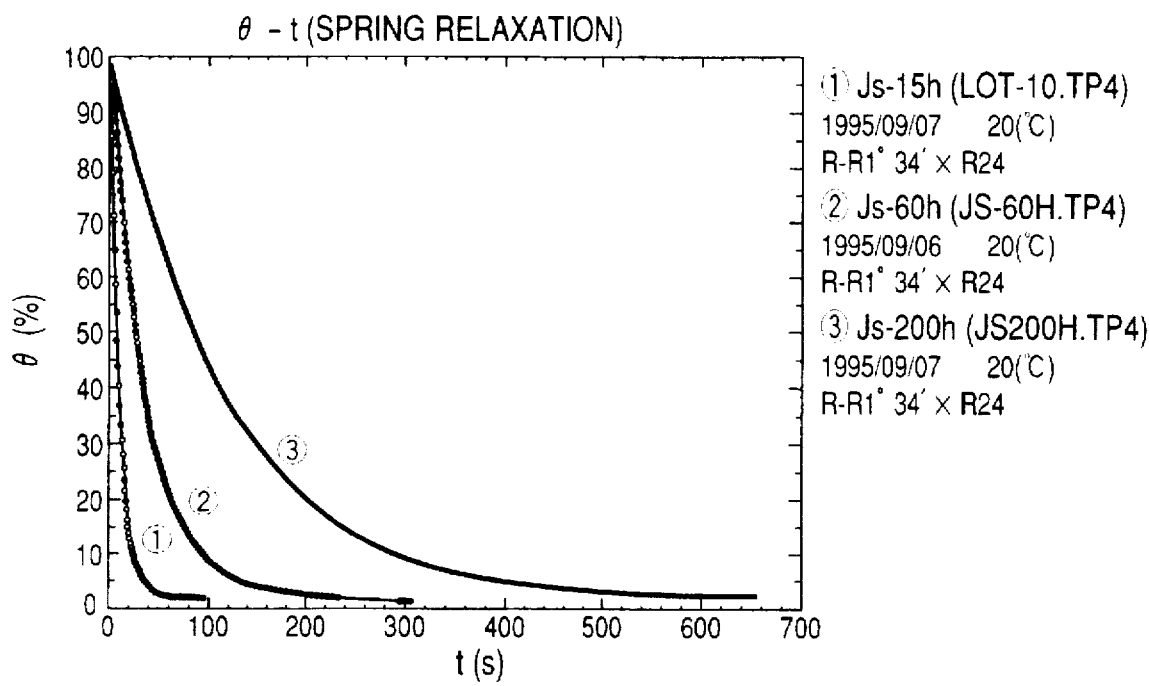
FIG. 21A is a spring relaxation graph obtained by the spring relaxation method in accordance with the present invention for standard liquids JS15H, JS60H, JS200H.
Figure 21B:
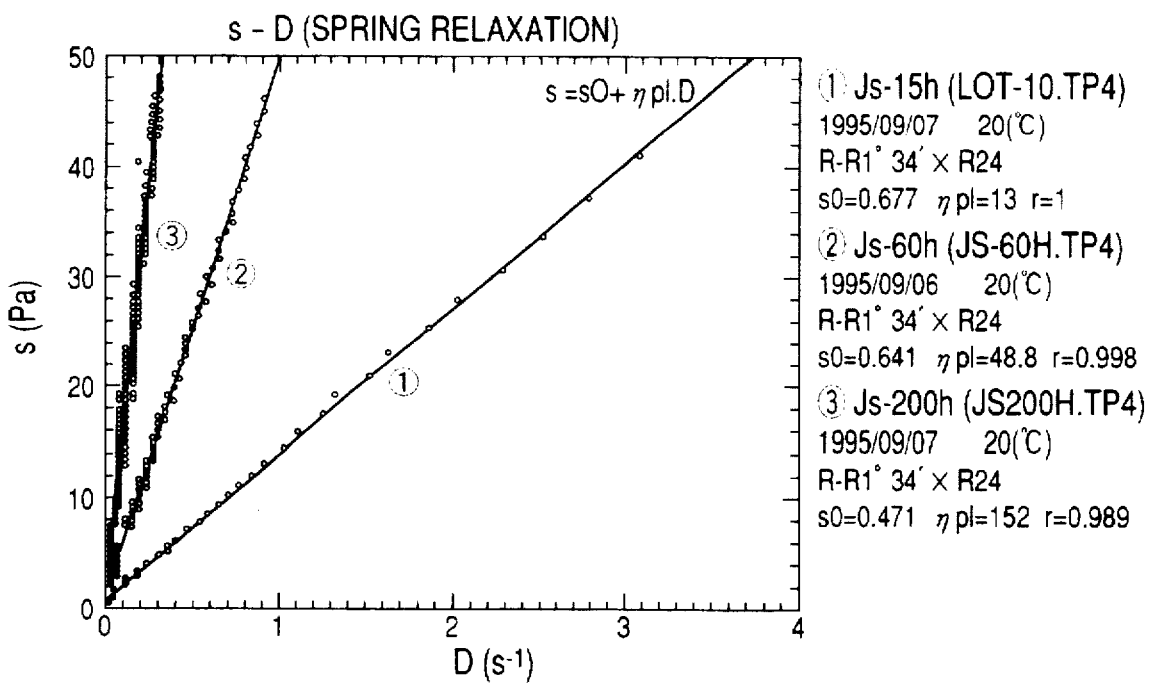
FIG. 21B is an s-D graph for the standard liquids based on FIG. 21A data.

FIG. 21A is a spring relaxation graph obtained for these samples at 20° C. FIG. 21B is an s-D flow graph for the shear stress s and the shear rate D obtained from data of the spring relaxation graph. Here numbers "1", "2" and "3" in the graphs indicate the curves for JS15H, JS60H and JS200H respectively.

As shown in FIG. 21B, data obtained for all the samples in the s-D flow graph are distributed along straight lines, all of which go through the graph origin. Viscosity values are calculated from gradients of these straight lines as $\eta p1=13$ Pa·s for the curve (1), $\eta p1=48.8$ Pa·s for the curve (2), and $\eta p1=152$ Pa·s for the curve (3). These measured viscosities are in good agreement with the test result data at 20° C. attached to standard liquids of 13.07 Pa·s for (1), 47.78 Pa·s for (2), 151.2 Pa·s for (3). The test result data of the standard liquid for calibrating viscometer are measured and provided by the National Reserch Laboratory of Metrology of Japan. Agreement of the measured data with the standard calibration data proves that the hypothesis described above is correct.

It is now obvious that the abnormality observed during the spring relaxation measurement for high viscous samples is caused by the rotor elevating operation of the rotor shaft auto-locking device at the start of the measurement. Another abnormality which is observed for high yield value samples as having different residual indications in the indicated value of the viscometer for different target values of the winding angle in the spring relaxation method, is caused in the same way as the abnormality for high viscous samples, and this will be described in the following.

Independent of the target value of the winding angle, the rotor shaft 5b elevated by the rotor shaft auto-locking device is released after completion of the winding up operation at the start of the spring relaxation measurement. When the rotor shaft 5b is released, it starts to move downward as the releasing operation progresses. When the rotor 6a moves down on the sample liquid 700, the same phenomena occur as for the case where the high viscous liquid is used as the sample liquid 700. Namely, the sample liquid 700 is able to make contact only with a part of a liquid contacting surface of the rotor 6a while the rotor 6a is sitting on the top of the sample liquid 700 as shown in FIG. 20B.

When the locking of the rotor shaft 5b is released in this condition and the recovery torque of the spring starts to be exerted, a viscous torque which may be generated in the measurement having an ideal contacting state or a damping torque due to the yield value would not be generated. This means that the recovery torque of the spring is quite small like in a case where the lower indicated value is set, and make it possible to rotate the rotor 6a even at torque levels with which the rotation is supposed to be stopped by the damping torque due to the yield value in the ideal measurement condition. Consequently, the rotor 6a is still able to rotate even at the target indicated value of the viscometer which is lower than a value of the residual indication obtained for the measurement with a 100% indicated value of the viscometer. Thus the measurement results indicate a lower value for the residual indication, and various yield values are obtained for different target indicated values of the viscometer according to different conditions.

Therefore it has become clear that the two abnormalities observed during the measurement are caused due to the elevating operation of the rotor shaft by the rotor shaft auto-locking device.

If the rotor shaft were to be locked without elevating it in order to remove the cause of the above abnormalities during the spring relaxation measurement, the pivot protecting function in the rotor shaft auto-locking device would be lost.

The present invention has the following characteristics to accomplish the spring relaxation measurement method mentioned above without losing the pivot protection function.

To provide both the pivot protection function and the spring relaxation measurement function, operational states of the rotor shaft auto-locking device in the viscometer according to the present invention include; a released state in which the rotor shaft is released for unlocking and the rotor is rotatably supported; and a locked state in which the torque detecting shaft is elevated and the pivot is separated from the jewel bearing for locking the rotor shaft; and further include a latched state as the third state of this device in which the rotor shaft is locked against the rotation but the torque detecting shaft has not been elevated, i.e. the rotor shaft is locked against the rotation, and the pivot is still in contact with, or substantially in contact with, the bearing.

Further in the present invention, control means of the viscometer is provided to have a plurality of measurement modes of different kinds for carrying out various operations to measure the viscosity of a sample liquid. Among those measurement modes, there is a mode for the spring relaxation measurement method according to the present invention. In this mode, the viscous property measurement of a sample liquid in an ultra-low shear rate range is made possible with the measurement operation comprising the steps of; driving a drive shaft connected to rotational driving means by operating the rotational driving means while the rotor shaft auto-locking device is in the latched state mentioned above; continuing the rotation to winding up an elastic member until output of a signal transformer, which detects an angular displacement of the drive shaft with respect to a torque detecting shaft which is extended from the rotor shaft, reaches 100% of the full scale indicated value of the viscometer or any other preset value; transferring the state of the viscometer to a state for executing the spring relaxation measurement in which the rotor shaft auto-locking device is operated after the completion of the winding up operation to unlock the locking of the rotor shaft and let the recovery torque of the elastic member drive the rotor; and collecting data on time variation of the indicated value of the viscometer with a constant time interval during a period where the indicated value of viscometer is gradually decreasing.

To apply the present invention to the rotor shaft autolocking device of the prior art for example, a latching position to rotatably support the rotor to accomplish the latched state described above may be added between a releasing position for rotatably supporting the rotor and a locking position for locking the rotor shaft.

Detecting means for detecting the latching position, for example, may be configured by attaching a light shielding plate to an elevating sleeve of a locking mechanism in the rotor shaft auto-locking device of the prior art, and detecting a position of the light shielding plate which moves up and down with the elevating sleeve by a position detector, such as a photo interrupter in which the detection is made using light and no physical contact is required.

Further in the present invention, the following operation sequence for a preparation process will be carried out utilizing the rotor shaft auto-locking device with the latching position to enable the measurement of various viscous properties in an' ultra-low shear rate range.

It is almost impossible for a sample liquid to make circumferentially uniform contact with the rotor's surface by just injecting a preset amount of the sample liquid between the cone rotor and the base plate for the spring relaxation measurement since the sample liquid stays between the cone rotor and the base plate as it is injected. A condition, in which the sample liquid is uniformly in contact with a whole area of the liquid contacting surface of the rotor and a surface of the base plate facing thereto, can be accomplished after rotating the rotor to increase affinity with the sample liquid.

Therefore the rotor should be rotated before the measurement in the spring relaxation method to increase affinity of the rotor and the base plate with the sample liquid. An operation to rotate the rotor for this purpose is called the running-in operation. The measurement of the steady flow method, on the other hand, is carried out with the rotor rotating continuously. Therefore the running-in operation as in the spring relaxation method is not required in the steady flow measurement.

Since the running-in operation before the start of the measurement is required in the spring relaxation method, the viscometer of the present invention is provided to be able to perform the running-in operation by driving the rotor to rotate at an arbitrary rotational speed while the rotor shaft is in the released state. Specifically, the viscometer of the present invention carries out an operation sequence comprising the steps of; pre-setting values of variables such as a rotational speed, and a period of rotation to determine a condition of the running-in operation; automatically executing the running-in operation with the preset condition when start of the measurement is instructed; and executing the spring relaxation measurement described above after the completion of the running-in operation.

Further in the present invention, the viscometer is able to carry out an operation sequence, similar to the running-in operation, for a sample liquid with thixotropic properties to study a recovery function of the sample whose structure was damaged by the shearing.

The operation sequence comprises; executing of the running-in operation in which the rotor is rotated at a preset rotational speed for a preset period; leaving the rotor shaft auto-locking device in a latched state for a preset leave-period; and transferring a state of the viscometer for the spring relaxation measurement.

Operation sequences of the running-in operation and the operation for recovering of the damaged structure by the shearing are explained with reference to timing charts in FIG. 22A and 22B respectively.

Figure 22A:
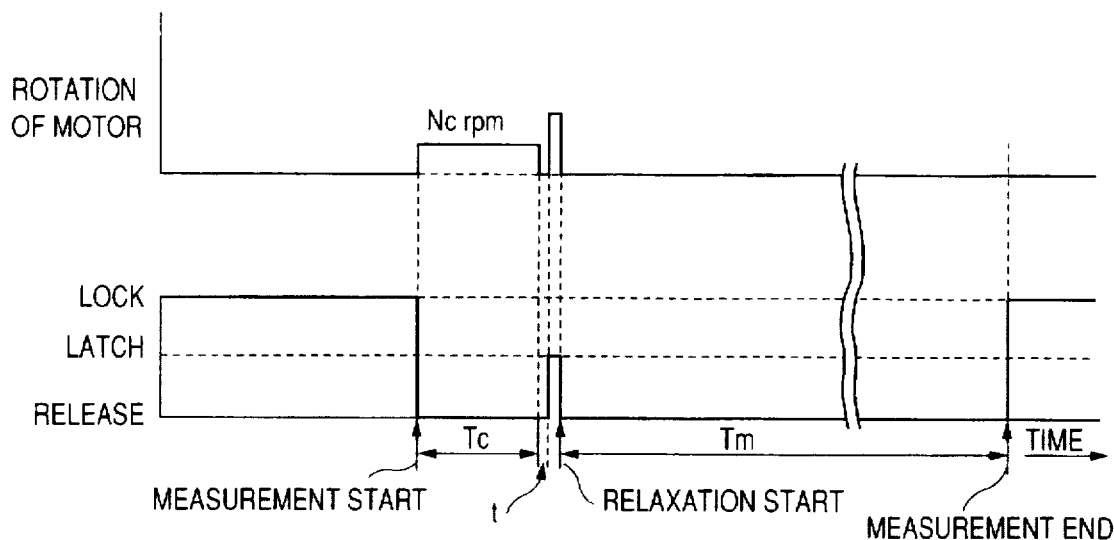
FIG. 22A is a timing chart showing an example of the running-in operation sequence.

When the running-in operation is executed prior to the spring relaxation measurement, the rotor shaft auto-locking device is in the locked state before the measurement start as shown in FIG. 22A. When the measurement start is instructed in this state, a state of the rotor shaft auto-locking device transfers to the released state. At the same time, the viscometer starts the rotor rotation with a preset rotational speed Nc for a preset period Tc to perform the running-in operation, and then stops the rotation after the completion of the running-in operation. For a typical case, a low rotational speed of about one rpm may be set for Nc, and a period in which the rotor can rotate twice or so with the low rotational speed may be set for Tc.

Then, the rotor shaft auto-locking device changes its state to the latched state to constrain the rotation of the rotor shaft. While mainitaining this state, the spring of the viscometer is wound up to 100% of the target indicated value or any arbitrary value designated. After the winding up of the spring, the rotor shaft auto-locking device changes its state to the released state to unlock the constraint of the rotor shaft, and then the spring relaxation measurement starts.

After an elapse of a measurement period Tm, the measurement is terminated and the rotor shaft auto-locking device returns to the locked state, i.e. the pivot protecting state.

A character t shown in the figures indicates a margin-period (about 20 seconds for example) for reducing the rotor speed so that the locking mechanism is geared with the rotor to lock the rotor rotation after a rotation of the driving motor has stopped.

Figure 22B:
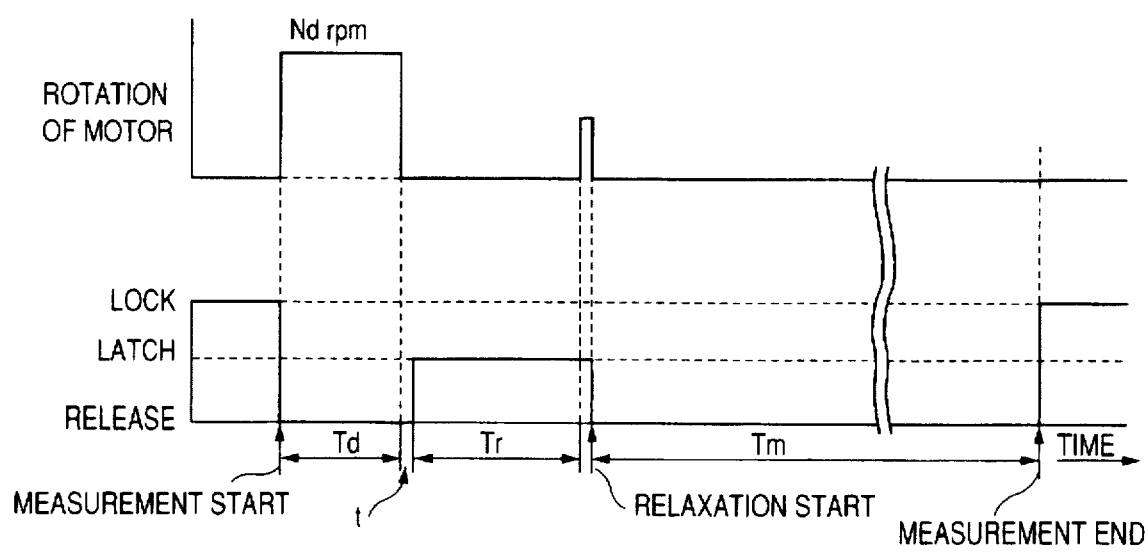
FIG. 22B is a timing chart showing an example of the operation sequence for studying a structural recovery process.

When the operation sequence for recovering of the damaged structure is executed prior to the spring relaxation measurement, a state of the rotor shaft auto-locking device is in the locked state before the. measurement starts, as shown in FIG. 22B.

When the measurement start is instructed, the state changes to the released state, and the shearing is applied on the sample liquid while rotating the rotor by the driving motor at a preset rotational speed of Nd. The rotation is terminated after an elapse of Td, a period of continuing rotation. The state changes to the latched state after a delay of t seconds, and is left for a leave-period of Tr for structural recovery. Then the spring relaxation measurement starts, the same as described in the case of FIG. 22A.

These two operation sequences for the preparation process may be treated as a single control mode in the control device of the viscometer. The operation sequence in FIG. 22A is equivalent to that of FIG. 22B if the leave-period Tr is set to zero.

In addition to the above operation sequence, the viscometer may have another control mode to execute an operation sequence in which the operation sequence of FIG. 22B is repeated while changing a value of the leave-period Tr for each operation and having a preset pause-period Ts between the operations. With this control mode, it is possible to examine a relationship between a recovery state of a sample structure and a value of the leave-period for the structural recovery, and thus to study a structural recovery process of the sample.

In addition to the running-in operation, the viscometer may still have another control mode to execute an operation, in which the rotor is rotated at a high rotation speed to break the structure of a sample intentionally, just before the spring relaxation measurement on the damaged sample starts. This control mode enables the study of effects of the structural damage on the spring relaxation measurement results. A degree of the structural damage on the sample may be changed by adjusting the rotation speed or the rotation period.

Having means to realize the new latched state in the rotor shaft auto-locking device according to the present invention, it becomes possible to eliminate the abnormalities observed during the spring relaxation measurement of the prior art and to execute the running-in operation and the operation for the structural recovery measurement. Therefore it is possible to provide a multi-purpose viscometer which is far more stable than the prior art and enables the measurement of viscous properties in an ultra-low shear rate range.

Preferred embodiments of the present invention will now be described with reference to relevant figures. In the following explanation the same numerics or symbols are used for the same parts throughout all the figures.

First, a configuration of a rotary viscometer in this embodiment is explained.

Figure 23:
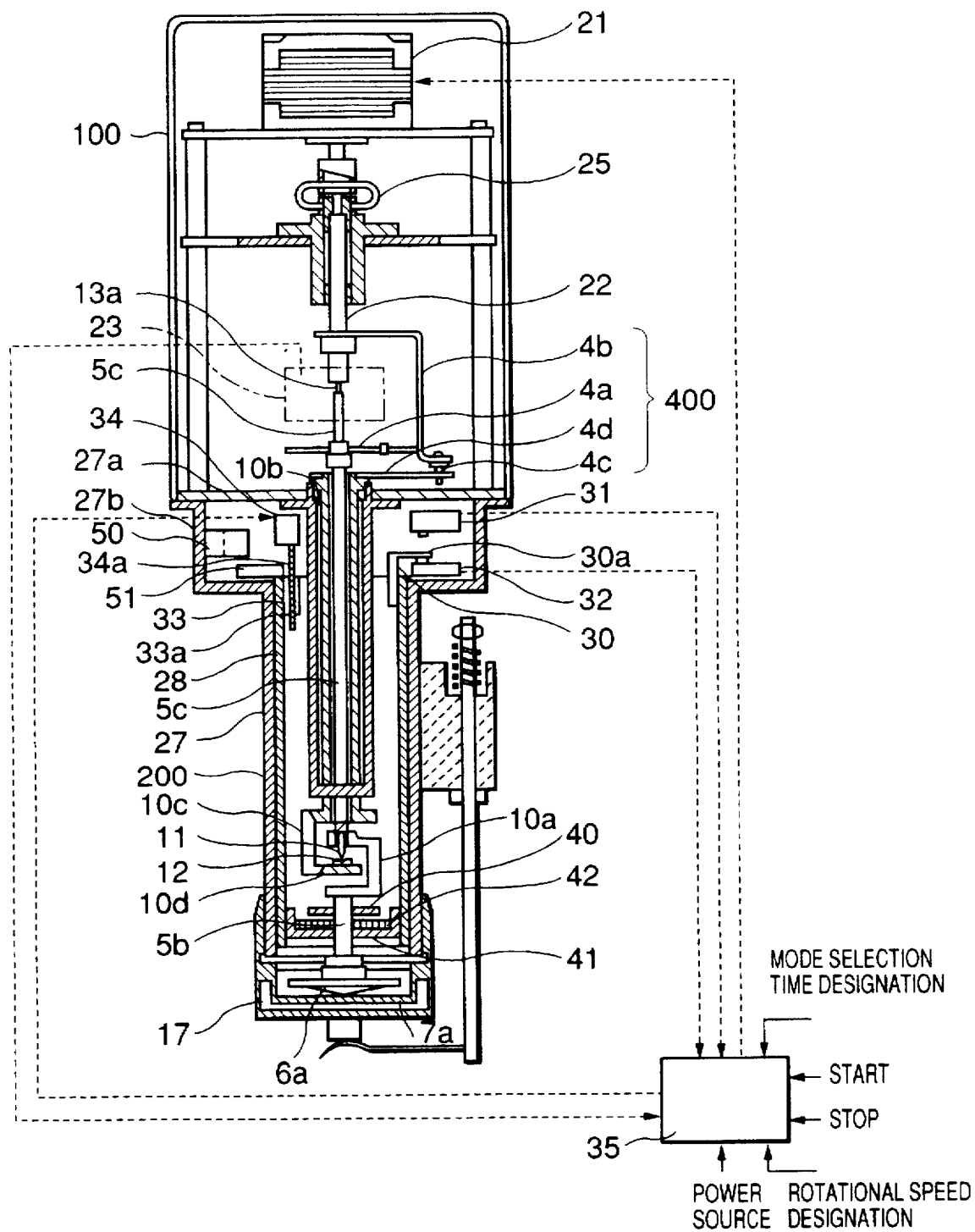
FIG. 23 is a longitudinal sectional view showing the structure of an embodiment according to a preferred rotary viscometer of the present invention.

As shown in FIG. 23, the rotary viscometer of the present embodiment comprises a plate 7a for holding a sample liquid; a jacket 17 which surrounds the plate 7a for keeping the sample liquid at a constant temperature; a cone-shaped rotor 6a; a rotor shaft 5b (a first driving shaft) for holding and rotating the rotor 6a; a main body 100 for driving the rotor 6a through the rotor shaft 5b and for measuring the viscosity; and a pivot protecting device 200 which forms rotor shaft locking means and is disposed between the main body 100 and the rotor 6a.

In this embodiment, a small portion at a peak top of the cone-shaped rotor 6a has been cut off to form a flat plane therein.

This is done because noise during measurement could be generated due to a friction torque if the peak top of the cone-shaped rotor were actually in contact with the plate 7a. In the following part of this specification, "the top of the rotor 6a " means an assumed peak top which has been cut off unless otherwise mentioned. Also, "a state where the cone-shaped rotor 6a and the plate 7a are in contact" in the measurement condition means a state where the assumed peak top of the cone-shaped rotor 6a is in contact with a surface of the plate 7a.

The main body 100 includes a driving motor 21, a rotary coupling 25 and an output shaft 22, which form rotary driving means; a second driving shaft 5c having a lower end linked with the rotor shaft 5b within the pivot protecting device 200; a first linking means 400 which elastically links the output shaft 22 with the second drive shaft 5c; and a rotary differential transformer 23 which performs functions of angular displacement detecting means between the output shaft 22 and the second driving shaft 5c.

The first linking means 400 includes an L-shaped member 4c having one end connected to a part in the vicinity of the lower end of the output shaft 22; and a spiral spring (torque spring) 4a disposed between the other end of the L-shaped member 4b and the second drive shaft 5c, connecting both parts elastically. The first linking means 400 further includes an arm member 4d, having one end linked with the L-shaped member 4b and the other end linked with a sleeve 10b which will be described hereafter, for transmitting a rotational drive force of the output shaft 22 to the sleeve 10b.

A pin 13a, which is rotatably inserted into a hole which is not shown in the figure and formed at the end face of the output shaft 22, for preventing the second drive shaft 5c from swinging, is fixed at the end face of the second drive shaft 5c.

The hole formed at the end face of the output shaft 22 has such a depth that a slight axial displacement of the pin 13a is allowed, i.e. a depth by which the axial displacement of the pin 13a corresponding to that of the rotor shaft 5b and the second drive shaft 5c can be absorbed.

The pivot protecting device 200 functions as the rotor shaft auto-locking device described above, and comprises a locking mechanism to constrain a rotational motion of the rotor shaft 5b and a pivot separating mechanism to separate a pivot 11 and a bearing 12, which will be described hereafter. Using these mechanisms, the pivot protecting device 200 realizes a released state in which the rotor shaft 5b is rotatably supported, a locked state in which the pivot 11 and the bearing 12 are separated and the rotor shaft 5b is locked, and a latched 15 state in which the rotor shaft 5b is locked while the pivot 11 is in contact with the bearing 12.

More concretely, the pivot protecting device 200 includes a pivot 11 and a bearing 12 which form means for rotatably bearing and supporting the rotor shaft; a channel-type linkage member 10a which functions as a second linkage means for linking the rotor shaft 5b with the second drive shaft 5c by bypassing the pivot 22 and the bearing 12; limit switches 31 and 32 functioning as first and second detecting means for detecting an operation state of the pivot protecting means, and an L-shaped fitting 30 for operating the limit switches 31 and The pivot protecting device 200 further includes a photo interrupter 50 and a light shielding plate 51 to trigger the photo interrupter 50. The photo interrupter 50 functions as a photo detector to accomplish non-contacting detection of a position which is disposed within a range between limits where the limit switches 31, 32 are turned on/off and is adjustable in a height direction. Most of these components are housed in a casing 27.

In this embodiment, the locked state of the pivot protecting device 200 is detected by the limit switch 31 (first detecting means), the released state is detected by the limit switch 32 (second detecting means), and the latched state is detected by the photo interrupter 50 (third detecting means). Specific means for detecting each state of the pivot protecting device 200 are not limited to these limit switches and the photo interrupter. Any other type of detecting means may be employed as long as it can detect and distinguish each state.

In the pivot protecting device 200, the pivot 11 is mounted on the lower end of the second drive shaft 5c while the bearing 12 is mounted on a lower side 10d of a channel type member 10c provided below the sleeve 10b which is disposed around the second drive shaft 5c. The pivot 11 and the bearing are coaxially mounted. The sleeve 10b is rotatably supported by an upper flange 27a of the casing 27. The arm member 4d is linked with the upper end of the sleeve 10b as mentioned above.

Figure 24:
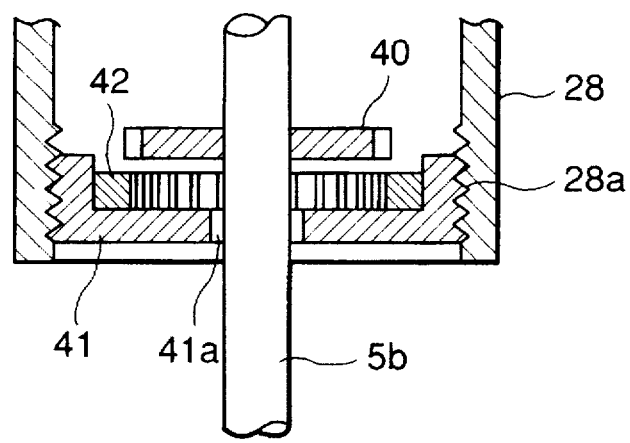
FIG. 24 is an enlarged view of the structure of the embodiment shown in FIG. 23.

A sleeve 28 is axially movably disposed within the casing 27 as shown in FIG. 24. The sleeve 28 is provided with an internal thread 28a in the lower portion thereof. The internal thread 28a is meshed with a disc 41. The disc 41 is provided with a through-hole 41a at the center thereof, through which the rotor shaft 5b can freely pass. The disc 41 is provided with a first engaging member, such as an internal threaded gear 42 on the upper side thereof. The rotor shaft 5b is provided with a second engaging member, such as an externally threaded gear 40, which is meshed with the internally threaded gear 42.

The externally threaded gear 40 is attached to the rotor shaft 5b in such a way that when the internally threaded gear 42 is displaced by the axial displacement of the sleeve 28, the externally threaded gear 40 is brought into mesh with the internally threaded gear 42 and then brought into contact with the displaced disc 41, and causing the externally threaded gear 40 to be secured to the rotor shaft 5b so that the gear 40 is axially displaced together with the rotor shaft 5b.

As shown in FIG. 23, a block 33 which is formed with a screw hole 33a is secured to the upper portion of the sleeve 28. A locking micro motor 34 is disposed at the flange 27a in a position opposite to the block 33. The micro motor 34 is provided with a threaded shaft 34a as an output shaft. The threaded shaft 34a is meshed with the screw hole 33a of the block 33.

The locking motor 34 rotates the screw shaft 34a in a normal direction or the reverse direction to displace the block 33 upwards or downwards. The sleeve 28 is displaced in an axial direction by the block 33.

The stroke of the displacement of the sleeve 28 is preset to a value which is necessary to separate the pivot 11 from the bearing 12. The stroke is preset to such a length that the internally threaded gear 42 is displaced so as to engage with the externally threaded gear 40 and the disc 41 is brought into contact with the externally threaded gear 40 to push the gear 40 upward for separating the pivot 11 from the bearing 12.

One side of the L-shaped fitting 30 is secured to the upper portion of the sleeve 28. The L-shaped fitting 30 is disposed in such a manner that the other side 30a projects outside of the sleeve 28 and is positioned between the limit switches 31 and 32 which have been described. In other words, the side 30a is disposed so that it may be displaced by the axial displacement of the sleeve 28 for turning the limit switches 31 and 32 on at the upper and lower limits of the displacement, respectively. Accordingly, the limit switches 31 and 32 are disposed in a spaced relationship corresponding to the stroke displacement of the sleeve 28 including the driving stroke of any one of the switches.

Figure 25:
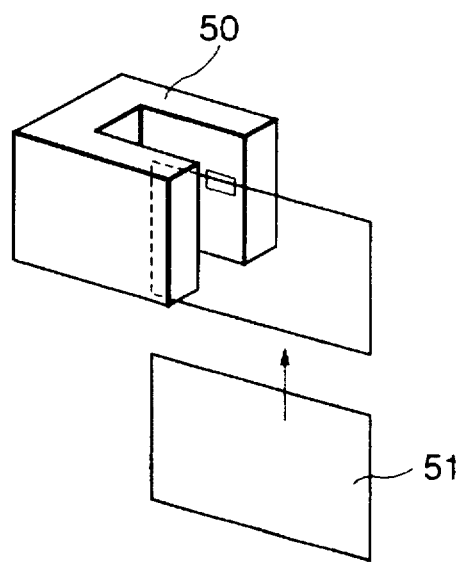
FIG. 25 is an explanatory view showing an example of the mechanism to detect the latched state.

Further, on the upper portion of the sleeve 28, the light shielding plate 51 for optically detecting a displacement is secured. As shown in FIG. 25, as the sleeve 28 moves upward, the shielding plate 51 moves into a detection gap of the photo interrupter 50, which is disposed at the upper portion 27b of the casing 27. The photo interrupter 50 includes a light source and a light detection device which are not shown in the figure. The light source and the light detection device is disposed in such a way as to set a light path in the detection gap to detect an insertion of the light shielding plate 51 as it interrupt the light path.

In this embodiment, the photo interrupter 50 is attached to the casing 27 in such a way that a height of the position of the photo interrupter 50 is adjustable from outside the casing 27. In this configuration, an elevation height of the sleeve 28 wherein the insertion of the light shielding plate 51 is detected, i.e. a height of the latching position, may be adjusted very easily.

Figure 26:
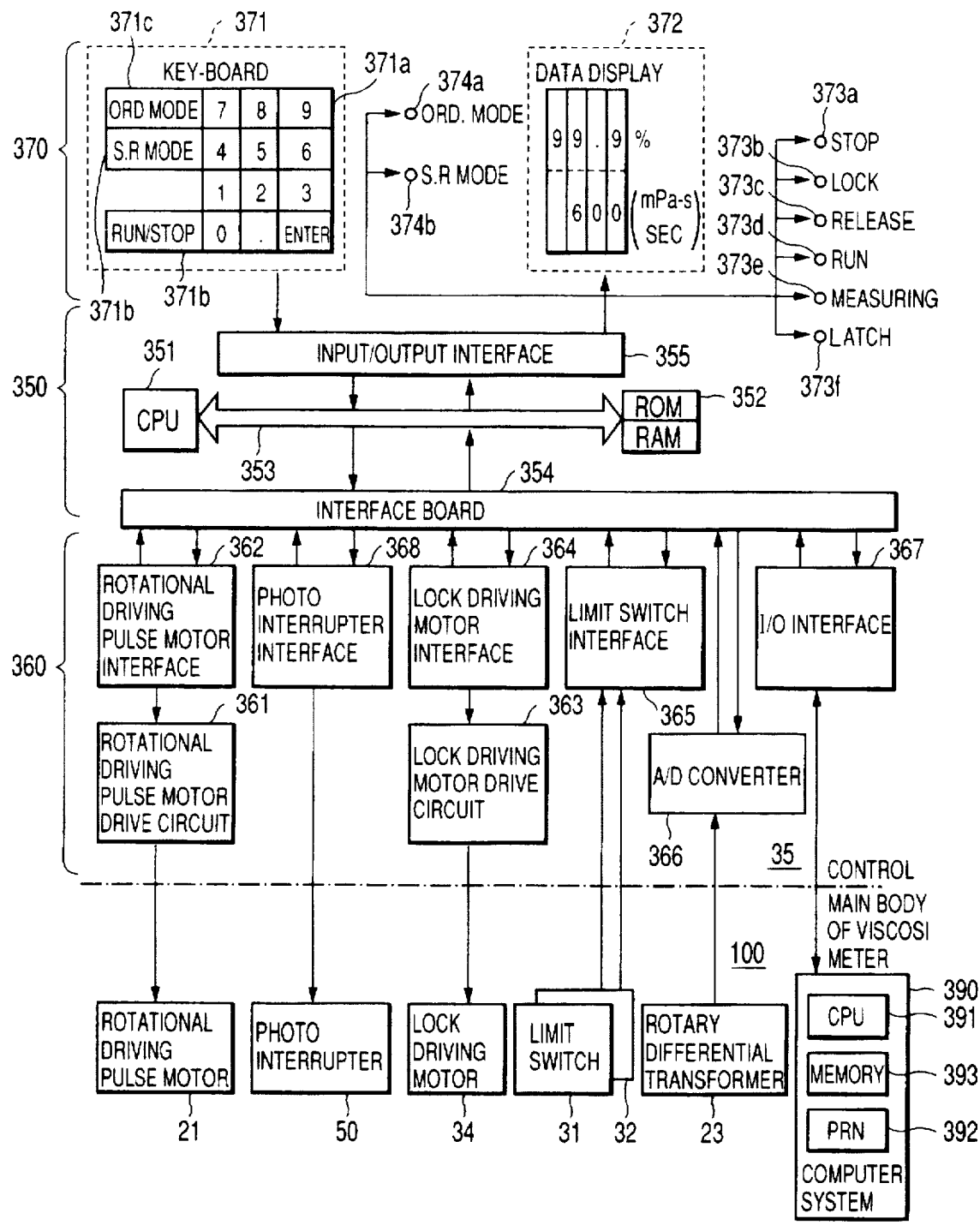
FIG. 26 is a block diagram showing an example of the system configuration of a control device in the embodiment shown in FIG. 23.

The viscometer in the present embodiment further includes a control device 35 for controlling the above mentioned mechanisms. The control device 35, for example as shown in FIG. 26, includes a drive control unit 360 which is connected with a main body 100 of the viscometer for transmitting and receiving measurement data and control signals; an information processing unit 350 for processing measurement data from the drive control unit 360 and for controlling the operation of a drive control system; and an input/output unit 370 for inputting/outputting information to and from the information processing unit 350.

The information processing unit 350 includes a central processing unit (CPU) 351 for executing control for the measurement of viscosity and executing the processing of the measurement data; a memory 352 for storing therein programs which are executed by the CPU 351, various data, results of processing, etc.; a data bus 353 and an interface board (IB) 354 for controlling input/output of the measurement data and control signals; and an input/output interface 355.

The memory 352 has a ROM (read only memory) for mainly storing programs, and a RAM (random access memory) for storing data.

One of the stored programs is, for example, a program for executing steps for measuring the viscosity using the spring relaxation method. In the following, the example steps of such a program will be described, where the running-in operation sequence (FIG. 22A) will be executed before the viscosity measurement.

(1) In the initial state, completing the selection of a control mode for executing the viscosity measurement by the spring relaxation method and the running-in operation sequence, and the entering of measurement condition variables such as a rotation speed Nc, a rotation period Tc for the running-in operation and a viscosity measurement period, and also stopping the rotor, i.e. setting the pivot protecting device 200 in the locked state, and detecting this state by the first detecting means (the limit switch 31);

(2) accepting an instruction to start a measurement after the above preparation step for measuring the viscosity by the spring relaxation method is completed;

(3) bringing the pivot protecting device 200 into the released state from the locked state by driving the constraining mechanism and the pivot separating mechanism until the second detecting means (the limit switch 32) detects that the pivot protecting device 200 is in the released state;

(4) after the completion of the transfer to the released state, driving the viscometer to rotate the rotor by operating the rotational driving means at the preset running-in rotational speed Nc (FIG. 22A), and continuing the driving operation for the preset running-in operation period Tc before the driving operation of the rotational driving means is stopped;

(5) operating the locking motor 34 to drive the locking mechanism until the third detecting means (the photo interrupter 50) detects the latched state in order to bring the pivot protecting device 200 from the released state to the latched state;

(6) after the completion of the transfer to the latched state, operating the rotational driving means to wind up the torque spring 4a while monitoring output of the differential transformer 23, and continuing the driving operation until the output reaches a value corresponding to 100% of the indicated value or any other preset target indicated value before the driving operation of the rotational driving means is stopped;

(7) operating the locking motor 34 until the second detecting means detects that the pivot protecting device 200 is in the released state to unlock the locked state of the locking mechanism and transfer the pivot protecting device 200 to the released state, and at the same time with the start of the transfer operation, turning the viscosity measurement means on to start a measurement operation;

(8) continuing the viscosity measurement operation for a preset measurement period in which measurement data are sent to the data processing means such as a personal computer at every preset constant interval, e.g. every one second interval, and stored therein; and (9) terminating the viscosity measurement operation after an elapse of the measurement period, and operating the locking motor 34 to drive the locking mechanism and the pivot separating mechanism until the first detecting means detects that the pivot protecting means has returned to the locked state, i.e. the state of pivot protection.

The operation sequence for the spring relaxation measurement with the running-in operation is described above. An operation sequence for measuring effects of the structural recovery of a sample liquid whose structure was damaged by shearing comprises the same operation sequence as that above except for the steps (1) and (4)–(7). Namely a program for executing the spring relaxation measurement including an operation sequence for the structural recovery executes the following steps;

(1) in the initial state, completing the selection of the control mode for executing the viscosity measurement by the spring relaxation method and the operation sequence for the structural recovery, and the entering of measurement condition variables such as a rotation speed Nd and a rotation period Td for the structural recovery operation, a leave-period Tr for the structural recovery and a viscosity measurement period, and also stopping the rotor, i.e. setting the pivot protecting device 200 in the locked state, and detecting this state by the first detecting means (the limit switch 31);

(2) and (3) are the same as steps (2) and (3) in the program for executing the spring relaxation measurement including the running-in operation;

(4) after the completion of the transfer to the released state, driving the viscometer to rotate the rotor by operating the rotational driving means at the preset rotational speed Nd (FIG. 22B), and continuing the driving operation for the preset operation period Td before the driving operation of the rotational driving means is stopped;

(5) operating the locking motor 34 to drive the locking mechanism until the third detecting means (the photo interrupter 50) detects the latched state in order to bring the pivot protecting device 200 from the released state to the latched state;

(6) maintaining the latched state for an elapse of the preset leave-period Tr after the completion of the transfer to the latched state, and operating the rotational driving means to wind up the torque spring 4a while monitoring output of the differential transformer 23, and continuing the driving operation until the output reaches a value corresponding to 100% of the indicated value or any other preset target indicated value before the driving operation of the rotational driving means is stopped; and (7) to (9) are the same as the steps (7) to (9) in the program for executing the spring relaxation measurement including the running-in operation.

Another example of the stored program is a program for measuring the viscosity by rotating the rotor at a constant speed. Ire this measurement mode, the following steps will be executed for example. This measurement mode is applicable to measurements of sample liquid properties with a viscosity changing in time, i.e. a measurement of so called time dependent sample liquids.

(1) In the initial state, completing a selection of a control mode for executing the viscosity measurement with a constant speed, and entering of measurement condition variables such as a rotation speed, a measurement time length and a recording data output interval, and also stopping the rotor of the viscometer, i.e. setting the pivot protecting device 200 in the locked state, and detecting this state by the first detecting means (the limit switch 31);

(2) accepting an instruction to start a measurement after the above preparation step of entering of the operation condition variables is completed;

(3) provided the pivot protecting device 200 is in the locked state, bringing the pivot protecting device 200 into the released state from the locked state by operating the constraining mechanism and the pivot separating mechanism by driving the lock driving motor 34, until the second detecting means (the limit switch 32) detects that the pivot protecting device 200 is in the released state;

(4) after completing the transfer to the released state, driving the rotational driving means to rotate the rotor of the viscometer at a preset rotational speed, and at the same time triggering the viscosity measurement means to start the measurement process;

(5) continuing the viscosity measurement for the preset measurement time length while outputting measurement data sampled during this period together with elapsed time data since the start of the measurement to an information processing device such as a personal computer or other type of data storage device, with a preset time interval designated as the recording data output interval; and (6) stopping the measurement after the preset measurement time length has elapsed, and operating the locking mechanism and the pivot separating mechanism to return to the states for pivot protecting by driving the lock driving motor 34 until the first detecting means detects the pivot protecting device 200 has entered the locked state.

The drive control unit 360 comprises a rotational driving pulse motor drive circuit 361 for driving the rotational driving motor 21; a rotational driving motor interface 362 for outputting a control signal from the information processing unit 350 to the drive circuit 361; a locking motor drive circuit 363 for driving the locking micro motor 34; a locking motor interface 364 for outputting a control signal from the information processing unit 350 to the locking motor drive circuit 363; a limit switch interface 365 for inputting on/off signals for the limit switches 31 and 32 to the information processing unit 350; a photo interrupter interface 368 for inputting on/off signal of the photo interrupter 50 to the information processing unit 350; an A/D converter 366 for analog/digital converting the measurement value of the rotary differential transformer 23 to send the converted value to the information processing unit 350; and an input/output interface 367 for connecting this control device with an external system, for example, a computer system. The computer system 390 includes, for example, a central processing unit (CPU) 391, a printer 392, a memory 393, etc.

The input/output unit 370 has a key-board 371 for externally inputting instructions to execute/stop, as well as data, to the control device 35, a data display 372 for displaying information outputted from the information processing unit 350, a status indicator 373 and a mode indicator 374.

The key-board 371 includes a numerical keypad 371a for inputting numerals; a run/stop switch 371b to instruct run or stop; and mode selecting keys 371c and 371d. The mode selecting key 371c selects an ordinary constant speed viscosity measurement mode (ORD MODE) in which the rotor is rotated at a constant speed, and the key 371d selects a spring relaxation viscosity measurement mode (S.R.MODE) in which the spring relaxation method is carried out.

When the spring relaxation viscosity measurement mode is selected, the key-board 371 further accepts input of the parameters such as the rotational speeds Nd, Nc, the rotation periods Td, Tc, and the leave-period Tr which are required for executing the running-in operation sequence or the operation sequence for the structural recovery, in addition to the target indicated value of the winding angle Θ and the measurement period Tm which are required for the spring relaxation measurement.

When the spring relaxation measurement with the preparation process is repeated to study the structural recovery process, the key-board 371 further accepts input of the repetition number K, a shift amount ΔT for reducing or increasing the leave-period Tr when the measurement is repeated and the pause-period Ts between the measurements. Here these parameters K, ΔT and Ts are normally set to default values of 1, 0 and 0 respectively. The repeating measurement will not be executed unless it is instructed. Specific operation steps for this measurement will be described later.

Data such as the measured indicated values of the viscometer, viscosity values, rotational speeds of the rotor, elapsed time are displayed in numerical form on the data display 372. The data display 372 may be comprised of a fluorescent display or a liquid crystal display.

Light emitting diode indicators 373a, 373b, 373c, 373d, 373e and 373f are disposed in the status indicator 373. The indicators 373a, 373b, 373c, 371d, 373e and 373f indicate states of stop, locked, released, run, measuring and latched respectively, and are illuminated depending upon the state of the viscometer.

The mode indicator 374 has an ordinary viscosity measuring mode indicator (ORD. MODE) 374a indicating the mode in which the rotor is rotated at a constant speed, and a viscosity measuring mode indicator (S.R.MODE) 374c indicating the mode in which the spring relaxing method is carried out.

The pivot protecting device 200 has the configuration mentioned in the above and attains the following three states, i.e. the locked state (the first state) in which the rotor shaft 5b is locked and the pivot 11 is separated from the bearing 12, the released state (the second state) in which the pivot 11 is in contact with the bearing 12 and locking of the rotor shaft 5b is released, and the latched state (the third state) in which, situated in between the first and second states, the rotor shaft 5b is locked but the pivot 11 is not separated from the bearing 12.

The control system 35 controls the driving of the locking micro motor 34 to bring the pivot protecting device 200 into a target state and controls the driving of the rotating driving motor 21 depending upon the target state.

Operation of the rotary viscometer in the present embodiment will now be described with reference to the flowcharts.

Figure 27:
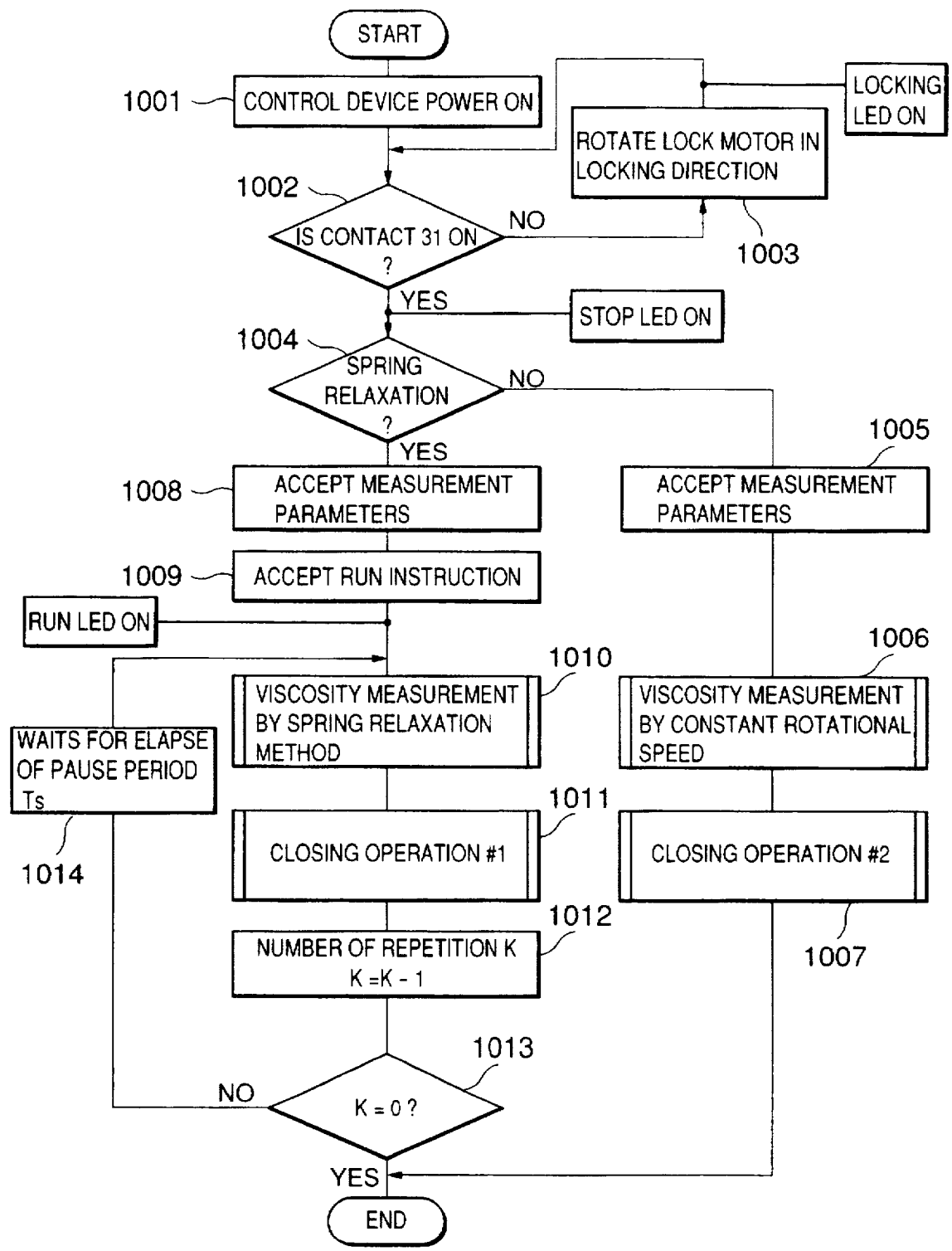
FIG. 27 is a flow chart showing an overview of the viscosity measurement operation in the embodiment shown in FIG. 23.

First, an overview of the measuring operation of the rotary viscometer in the present embodiment will be described with reference to FIG. 27.

When, the power of the control system 35 is turned on for starting the measurement (step 1001), the CPU 351 checks whether or not the contacts of the limit switch 31 are turned on (step 1002). This can be detected by a signal from the limit switch interface 365. If the limit switch 31 is turned off, the locking operation is executed.

More concretely, the locking motor drive circuit 363 is instructed to drive the locking motor 34 in such a direction as to lift up the sleeve 28 via the locking motor interface 364 (step 1003). At this time, the CPU 351 lights the indicator 373b until the limit switch 31 is turned on. If the limit switch 31 is already turned on, the locking motor 34 is not driven.

When the locking motor 34 is driven, the screw 34a is rotated. The block 33 which is meshed with the screw 34a is axially displaced by the rotation of the screw 34a so that the sleeve 28 to which the block 33 is secured is moved upward. When the sleeve 28 is moved upward, the disc 41 to which the sleeve 28 is secured is also moved upward. The internally threaded gear 42 which is provided on the disc 41 is brought into threadable engagement with the externally threaded gear 40 secured to the disc 41 by the upward movement of the disc 41. This causes the rotor shaft 5b to be locked against rotation by the sleeve 28. Further upward movement of the sleeve 28 causes the disc 41 to push up the externally threaded gear 40. This causes the rotor shafts 5b and 5c to be pushed for moving the pivot 11 upward so that the pivot 11 is separated from the bearing 12.

This operation causes the rotor shaft 5b to be locked and causes the pivot 11 to be separated from the bearing 12. The locking of the rotor shaft 5b and separation of the pivot 11 from the bearing 12 is also performed upon completion of measurement as will be described hereafter.

Then, determination of the measuring mode is made (step 1004). Measuring mode determination is made by checking which of the mode selecting keys 371c and 371d is selected. If the viscosity measurement by the constant speed rotation method is selected, measurement parameters for this mode are accepted (step 1005), and then the measurement in this constant speed mode is carried out (step 1006), and finally a closing operation #2 is carried out (step 1007) to complete the measuring operation.

If the spring relaxation method is selected, measurement parameters for this measurement mode are accepted (step 1008). Such parameters include, for example, a target indicated value Θ of the winding angle and a measurement time length Tm; a rotational speed Nd, a rotation period Td and a leave-period Tr for preparation steps; a repetition number K, a shift amount ΔT for reducing or increasing the leave-period Tr when the measurement is repeated and a pause-period Ts between the measurements for the repetition measurement. Alternatively, accepting of the measurement parameters may be done immediately after the power of the viscometer is turned on, together with the locking operation of the rotor.

An instruction to start the viscosity measurement, i.e. a run instruction is accepted (step 1009). When the run instruction has been accepted, the spring relaxation viscosity measurement with a preparation process comprising the running-in operation sequence or the operation sequence for the structural recovery is executed in response to the acceptance of the run instruction (step 1010). After the completion of the measurement, the closing operation #1 is executed (step 1011).

Next, it is determined if the spring relaxation measurement of step 1010 should be repeated or not. A value of the repetition number K is reduced one by one (step 1012), and the resultant value is checked if it is more than zero (step 1013). If it turns out to be the NO case in step 1013, steps 1010-1013 are repeated having the pause-period Ts (step 1014) in between. And if YES in step 1013, the measurement is ended assuming the measurement is repeated for the designated time. The pause-period Ts is set to a constant value in this case, and it may also be changed as the measurement progress.

Figure 28:
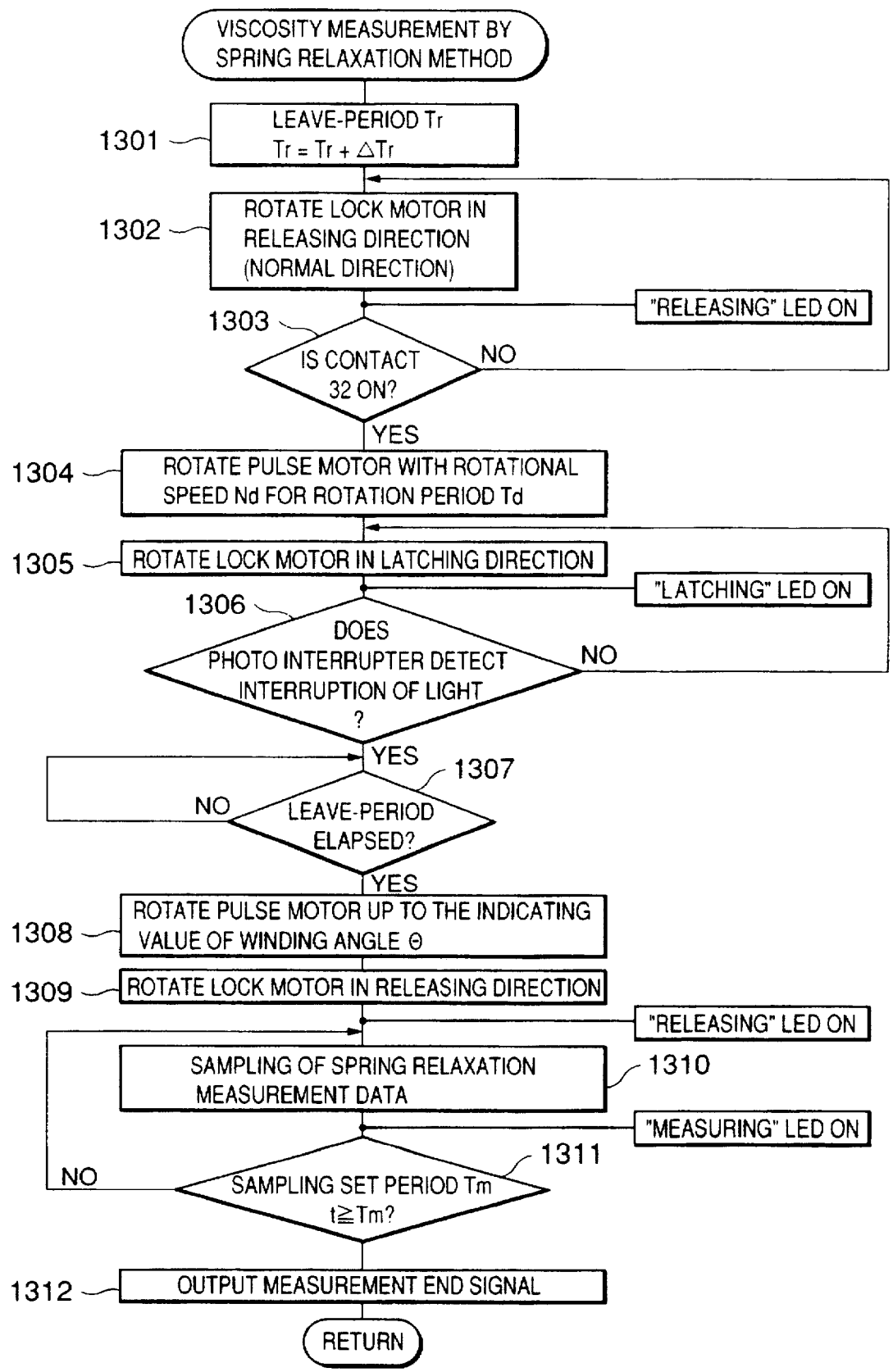
FIG. 28 is a flow chart showing the viscosity measurement operation using the spring relaxation method with the preparation process in the embodiment shown in FIG. 23.

Now, the viscosity measurement operation using the spring relaxation method with the preparation process, executed at step 1010 of FIG. 27 will be described with reference to the flow chart of FIG. 28.

At first, the leave-period Tr in the spring relaxation viscosity measurement is set by adding a preset shift amount ΔTr to the leave-period which had been set previously or an initial value of the leave-period (step 1301). In the present embodiment, the leave-period is shifted each time the measurement is repeated to study the time dependency of the structural recovery property of the sample. In the present embodiment, the leave-period is increased with the amount of ΔTr every time the measurement repeated. Alternatively the leave-period in the present invention may be set by selecting a large initial value and decreasing it gradually, or by multiplying a preset constant to a value of the repetition number K.

The CPU 351 activates the locking drive motor drive circuit 363 for driving the locking drive motor 34 in a releasing direction (step 1302). The CPU 351 continues this releasing operation until the limit switch 32 is turned on (step 1303) and lights the indicator 373c.

In other words, the locking drive motor 34 is driven to lower the sleeve 28 in the releasing operation. When the locking motor is driven, the screw 34a is rotated. The block 33 which is meshed with the screw 34a is axially displaced by the rotation of the screw 34a so that the sleeve 28 to which the block 33 is secured is lowered.

When the sleeve 28 is lowered, the disc 41 which is secured to the sleeve 28 is lowered. The externally threaded gear 40 which has been pushed up by the disc 41 is lowered by the lowering of the disc 41 so that the pivot 11 is lowered to make contact with the bearing 12. The internally threaded gear 42 is disengaged from the externally threaded gear 40 so that the locked state of the rotor shaft 5b by the sleeve 28 is released.

When the limit switch 32 is turned on, the releasing operation is stopped to carry out the spring relaxation viscosity measurement. At this phase, the rotor shaft 5b is rotatable and the pivot 11 is in contact with the bearing 12.

Then, the preparation process is executed (step 1304). The CPU 351 controls the rotational driving pulse motor 21 to rotationally drive at a preset rotational speed Nd for a preset rotation period Td.

The CPU 351 activates the lock driving motor drive circuit 363 for driving the locking drive motor 34 in a latching direction (step 1305). The CPU 351 continues this latching operation until a light path in the photo interrupter 50 is shielded by the light shielding plate 51 (step 1306) and lights the indicator 373f.

In other words, the locking drive motor 34 is driven to lift up the sleeve 28 in the latching operation which is opposite to the releasing operation. When the locking motor 34 is driven, the screw 34a is rotated. The block 33 which is meshed with the screw 34a is axially displaced by the rotation of the screw 34a so that the sleeve 28 to which the block 33 is secured is moved upward.

When the sleeve 28 is moved upward, the disc 41 which is secured to the sleeve 28 is also moved upward. As the disc 41 moves upward, the internally threaded gear 42 which is provided in the disc 41 is brought into threadable engagement with the externally threaded gear 40 which is secured to the rotor shaft 5b. Here, the sleeve 28 is configured so that it cannot rotate around its rotational axis as described above. Therefore the rotor shaft 5b is locked by the sleeve 28.

In this phase, the rotor shaft 5b is locked from the rotation, and the pivot 11 is in contact with the bearing 12.

After the completion of the transfer operation to the latched state, this latched state is maintain for the preset leaveperiod Tr for the structural recovery (step 1307). And after an elapse of the leave-period Tr, step 1308 is executed for the spring relaxation viscosity measurement.

In the spring relaxation measurement, the CPU 351 controls the rotational driving pulse motor 21 to wind up the torque spring 4a until the indicated value of the winding angle of the torque spring 4a becomes the target indicated value Θ while the latched state is being maintained (step 1308).

More specifically, the winding angle θ of the spring 4a detected by the rotary differential transformer 23 is converted into a digital value by the A/D converter 366 and is sent to the CPU 351. The CPU 351 compares the winding angle θ of the spring 4a with the target value Θ and activates the rotational driving pulse motor drive circuit 361 depending upon the result of the comparison for controlling the rotation of the rotational driving pulse motor 21.

Here the indicated value of 100% or any other value inputted by the numeric keys 371a of the keyboard 371 may be used as the target indicated value Θ. The input value is stored in RAM for example, together with information regarding the mode selection and the measurement parameters, the CPU 351 executes various judgement operations according to the information stored in RAM.

In step 1309, the releasing operation is executed in the same way as in step 1302 to transfer from the latched state to he released state and to unlock the constraint of the rotor shaft 5b. When the rotor shaft 5b is unlocked, the rotor 6a starts to rotate, driven by the relaxation torque of the spring 4a which has been wound up. The rotor 6a continues to rotate for a while against the viscous torque of the sample liquid.

In this embodiment, the change in the indicated value during the rotation of the rotor 6a driven by the relaxation torque of the spring 4a is detected by the rotational differential transformer 23. The CPU 351 samples the indicated value data from the rotational differential transformer 23 via the A/D converter 366 with a preset frequency as spring relaxation measurement data (step 1310).

During this period of time, the CPU 351 compares the period of time t lapsed since the start of measurement with the predetermined sampling period Tm (step 1311). If t<Tm, the measuring operation is continued and the indicator 373e is lit for this operation. If t≧Tm, a measurement end signal is outputted to terminate the measurement (step 1312).

The sampling interval and the sampling period can be registered in advance by means of the keyboard 371. The selected sampling interval is, for example, from one to several seconds. The selected sampling period is, for example, from five to ten minutes. Registration can be made in the RAM of the memory 352. The lapsed period of time t can be determined, for example, by providing a timer for counting the lapsed period of time. The sampling period Tm may be preset in the timer. In this case, comparison of T with t is not necessary. Measurement may be terminated at the time when a terminating signal is outputted from the timer.

The spring relaxation data is stored, for example, in the RAM of the memory 352. Operation for determining the viscosity is performed based upon the stored data. A result of the operation is stored in the RAM and displayed in the data display 372.

Alternatively, the measurement data may be sent to the computer system 390 and temporarily stored in the memory 393. Operation to determine the viscosity can be performed by the CPU 391 based upon the stored data. In this case, the result can be printed out by a printer 392 of the computer system. The result can be displayed in numerical, graphical or other form on a display (not shown).

Figure 29:
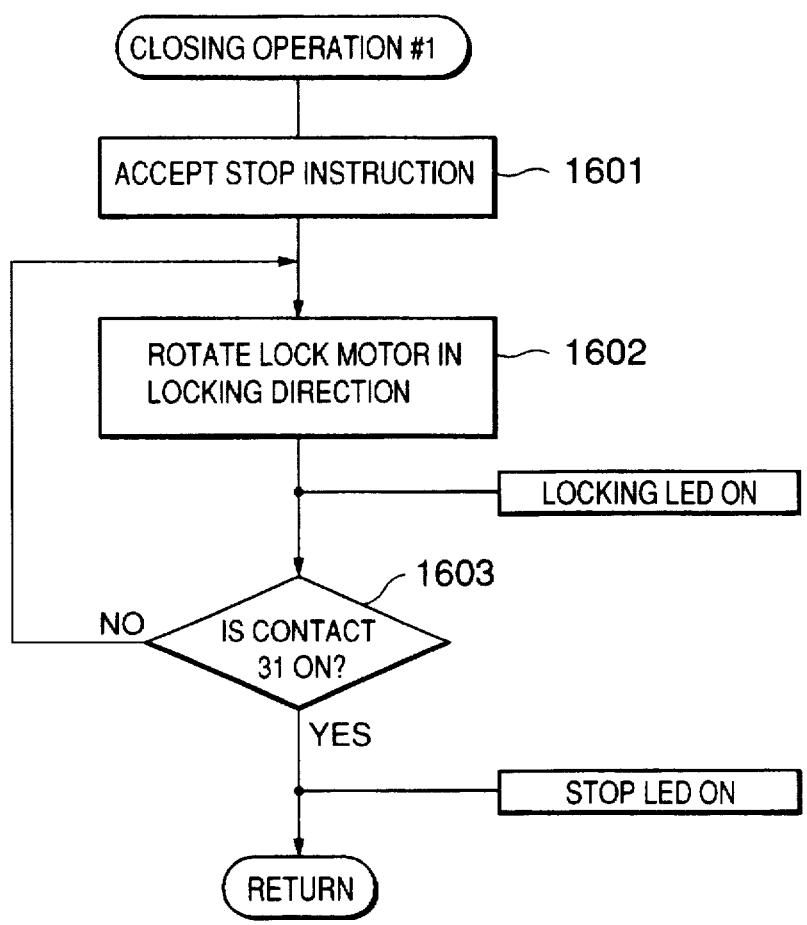
FIG. 29 is a flow chart showing the closing operation #1 in the embodiment shown in FIG. 23.

Thereafter, the measurement closing operation #1 of step 1011 in FIG. 27 will be explained with reference to a flow chart shown in FIG. 29.

This operation begins with reception of a stop instruction (step 1601). The stop instruction is made in response to the measurement end signal when the measurement is conducted by the spring relaxation method. If the CPU 351 receives the stop instruction, the CPU 351 controls the locking drive motor drive circuit 363 to drive the locking drive motor 34 in such a direction that the rotor shaft 5b is locked, i.e. the sleeve 28 is moved upward (step 1602). This control is continued until the limit switch 31 is turned on (step 1603). During this period of time, the indicator 373b is lit. When the limit switch 31 is turned on, driving of the locking drive motor 34 is stopped and the indicator 373a is lit.

Figure 30:
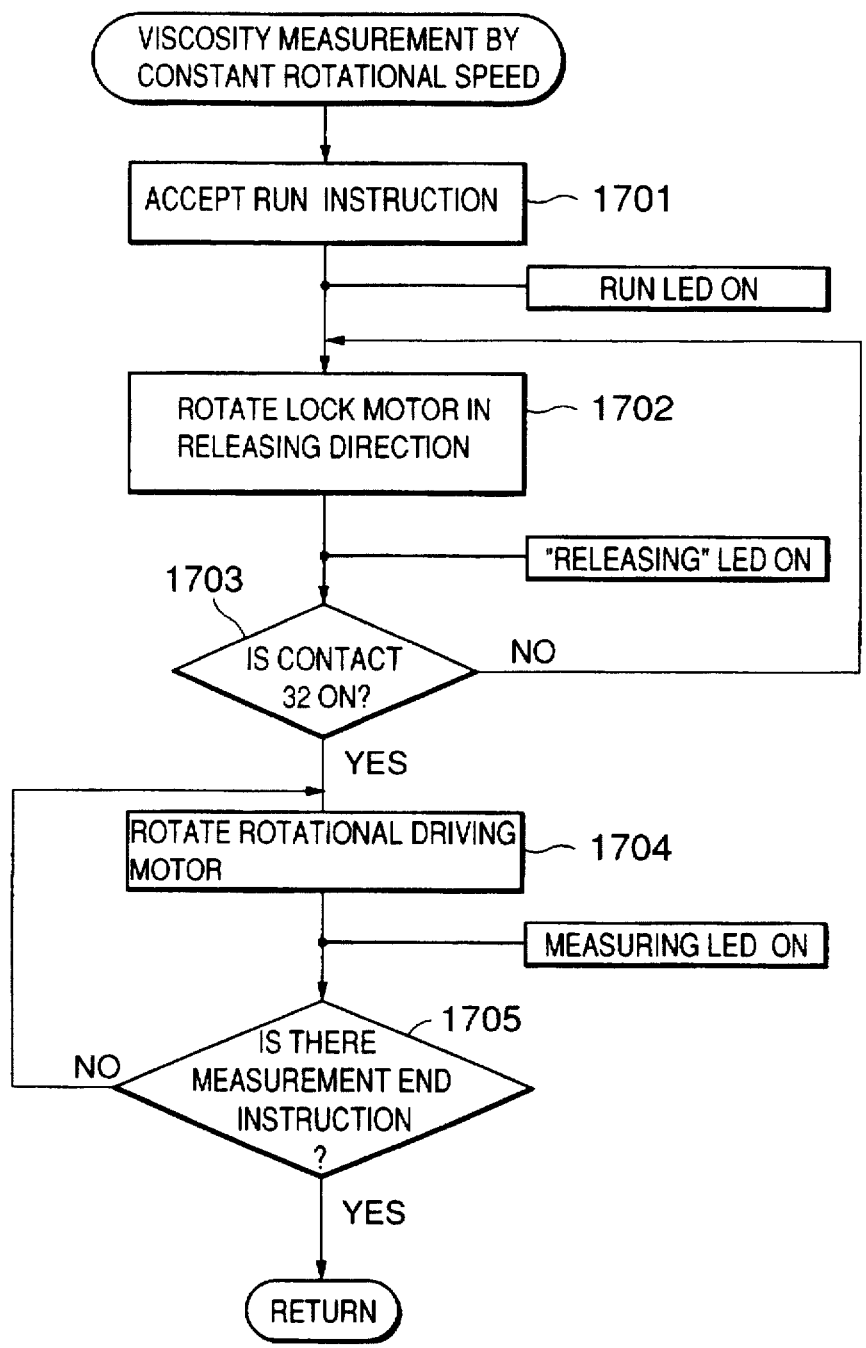
FIG. 30 is a flow chart showing the viscosity measurement operation using the constant rotational speed method in the embodiment shown in FIG. 23.

Now, operation for measuring the viscosity by the constant speed rotation method executed at step 1006 of FIG. 27 will be described with reference to a flow chart of FIG. 30.

An input instruction for measurement execution is accepted (step 1701). If there is an execution instruction, the CPU 351 receives it and instructs the driving of the locking motor 34 in such a direction that the sleeve 28 is lowered (step 1702). The releasing operation is continued until the limit switch 32 is turned on. During this operation, the CPU 351 lights the indicator 373c. If the limit switch 32 is turned on, the releasing operation is stopped to light the indicator 371d (step 1703). The CPU 351 instructs the rotational driving motor drive circuit 361, via the rotational driving motor interface 362, to rotate the rotational driving motor 21 (step 1704). The rotational speed can be specified and changed as mentioned above.

Measurement of the viscosity is conducted in this state. Measurement is performed by detecting the angular displacement between the output shaft 22 and the second drive shaft 5c by means of the rotary differential transformer 23. The value detected by the rotary differential transformer 23 is converted into a digital value by the A/D converter 366 and is sent to the information processing unit 350 via the interface board 354.

The measurement data are stored in, for example, the RAM of the memory 352 and operated on by the CPU 351. The operation result is displayed on the data display 372 together with the rotational speed of the rotor which is separately determined.

Also in this case, the measurement data may be sent to the computer system 390 and temporarily stored in the memory 393. Operation for determining the viscosity by the CPU 391 may be performed based upon the stored data. The operation result can be printed out by the printer 392 of the computer system. Alternatively, it may be displayed on a display (not shown) in numerical or graphical form.

Figure 31:
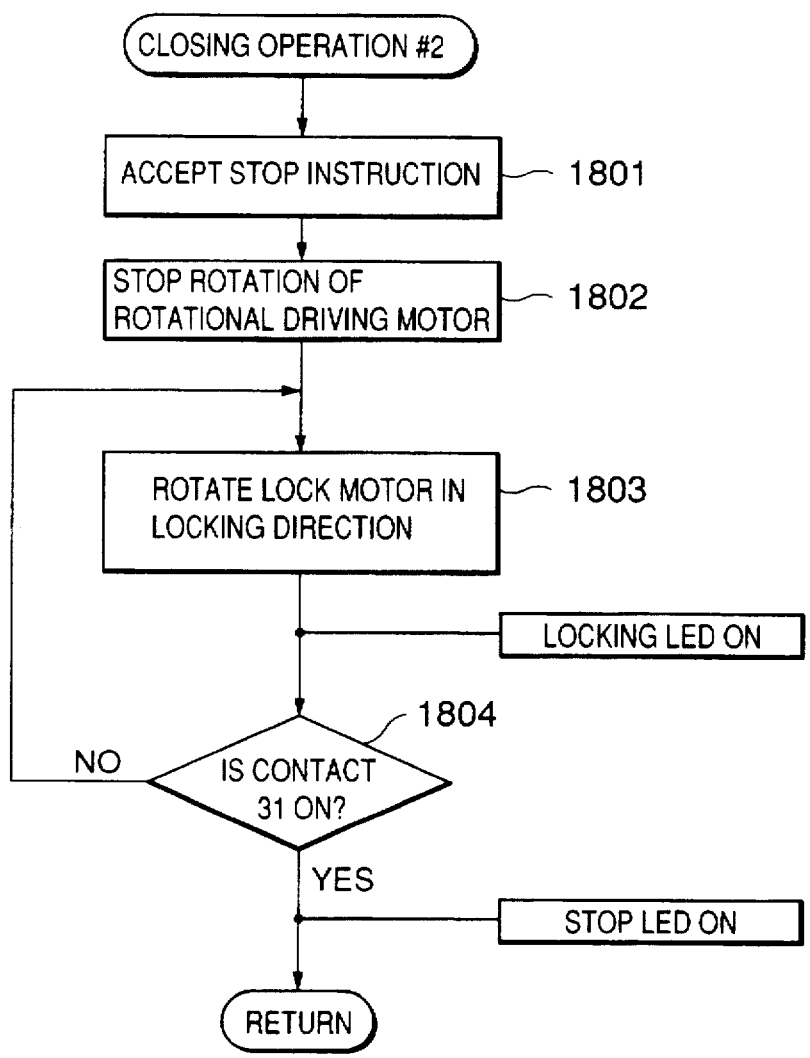
FIG. 31 is a flow chart showing the closing operation #2 in the embodiment shown in FIG. 23.

The closing operation #2 executed at step 1007 of FIG. 27 will now be described with reference to a flow chart shown in FIG. 31.

A stop instruction is received while the rotational driving motor is rotating and the indicator 371d is illuminated (step 1801). This stop instruction is made by input of a stop operation at the run/stop switch 371b. If stop is instructed, the CPU 351 sends an instruction to the rotational driving motor drive circuit 356 via the rotational driving motor interface 362 for stopping the rotational driving motor 21 (step 1802).

The CPU 351 then instructs the locking motor drive circuit 363 via the locking motor interface 364 to drive the locking motor 34 in such a direction that the sleeve 28 is moved upward (step 1803). The locking operation is continued until the limit switch 31 is turned on. During this operation, the CPU 351 lights the indicator 373b. The CPU 351 stops the locking operation and lights the indicator 373a if the limit switch 31 is turned on (step 1804).

The series of operations for measuring the viscosity by the constant speed rotation method is thus completed.

In the present embodiment the motor shaft 5b is locked against rotation after completion of the spring relaxation viscosity measurement and the constant rotational speed viscosity measurement. Also, the pivot 11 is separated from the bearing 12. Accordingly, the pivot can be protected from being damaged even when the rotor 6a is washed or replaced. Since the closing operation is sequentially and automatically performed in response to only one instruction of the measurement end until the protection of the pivot, a user will never wash the rotor without locking, even they forget about the locking. Since the state of the viscometer is displayed in the present embodiment, a user can easily recognize the state of operation of the viscometer and wrong operation can be prevented.

Furthermore in the present embodiment, the simultaneous execution of a locking or releasing operation and the viscosity measurement operation can be prevented since the driving of the rotational driving motor is prohibited when the locking motor is being driven.

Furthermore in accordance with the structure of the present invention, the viscosity measurement for the analysis of the viscous properties of the sample liquid in an ultra-low shear rate range using the spring relaxation method can also be sequentially and automatically performed except for initially charging the sample liquid into the viscometer.

Although the sleeve is displaced by means of the locking motor in each of the foregoing embodiments, the displacing method is not limited to this method. The displacement can be performed, for example, by using a linear motor, a solenoid, etc. as an actuator. The limit switch may be an optical switch, magnetic switch, pressure sensitive switch, etc. without being limited to a micro-switch. A micro switch, an electro/magnetic switch or the like may be used as means for detecting the relative position of the sleeve instead of the photo interrupter.

The present invention is not limited to only the above-mentioned embodiments and may be embodied in any other manner so that similar functions are performed. Various changes and additions of the present invention are possible within the scope of the disclosed technical concept.

As described above, in the present embodiment, the latched state is newly added in the rotor shaft auto-locking device (the pivot protecting device) of the prior art, and the function of the pivot protecting device of the prior art is improved so that the winding-up operation of the spring for the spring relaxation measurement is executed while the pivot protecting device is in the latched state.

Furthermore in the present embodiment, the running-in operation for increasing affinity between the rotor and the sample liquid or the preparation operation for executing the property measurement of the structural recovery process after the sample liquid is damaged by shearing can be automatically executed prior to the operation sequence of the spring relaxation measurement. These functions are newly introduced and are not included in the conventional viscometer for measuring using the spring relaxation method.

Because of these operations and functions, problems in obtaining accurate solutions for a high viscous sample and a high yield value in the conventional viscometer, with functions for executing the spring relaxation measurement in which the spring is wound up while the rotor is locked as it is separated from a plate standing still, can be resolved. Furthermore, not only the accurate measurement using the spring relaxation method in an ideal state, but also the measurement of physical properties such as studying of the structural recovery process can be easily accomplished.

Furthermore, the present invention can provide an excellent viscometer including the pivot protecting function which makes it possible to be handled the viscometer more safely for the conventional steady flow viscosity measurement, in the same way as in the viscometer of the prior art.

According to the present invention, a rotary viscometer can be provided so that the spring relaxation measurement can be executed accurately even for a high viscous sample or a high yield value sample with which the abnormalities are observed during the measurement using the conventional spring relaxation method, in the same way as for the measurement of a lower viscous sample and a lower yield value sample.

Further according to the present invention, a rotary viscometer can be provided so that the contacting states between the sample liquid and the rotor, and between the rotor and the plate can be improved, and the spring relaxation measurement can be executed with an ideal state.

Further according to the present invention, a rotary viscometer can be provided so that various preparation operations such as the running-in operation, operations for studying effects of the shearing hysteresis or the structural recovery can be executed prior to the viscosity measurement.

What is claimed is:

1. A rotary viscometer which measures information regarding rheological properties of a liquid sample using a spring relaxation method, comprising:

a rotor which is driven to rotate while contacting with a sample liquid to be measured;

a rotor shaft which supports said rotor and is a first drive shaft for transmitting a rotational drive force to said rotor;

rotational driving means having a drive power source, for driving said rotor to rotate and an output shaft for outputting the drive power;

a second drive shaft for transmitting the drive power to said rotor shaft;

a first linking means having an elastic member for elastically linking said output shaft with said second drive shaft via said elastic member so as to transmit the drive power therebetween;

support means having a pivot and a bearing for rotatably bearing and supporting said rotor shaft;

a second linking means which bypasses said support means for linking said rotor shaft with said second drive shaft;

indicated value detecting means for detecting an indicated value of said viscometer;

viscosity calculating means for calculating the viscosity from resultant indicated values during a measurement state;

pivot protecting means having a locking mechanism for locking and unlocking said rotor shaft against and for rotating, respectively, and a pivot separating mechanism for separating and contacting the pivot of said support means from and with the bearing, respectively; and control means for controlling operations of said rotational driving means and said pivot protecting means, wherein said indicated value detecting means detects rotational angular displacements between said rotor shaft and said second driving shaft, which correspond to said indicated values of said viscometer;

said pivot protecting means realizes three states, a first state in which said rotor shaft is locked against rotating and said pivot of said support means is separated from said bearing, a second state in which said pivot of said support means is in contact with said bearing and locking of said rotor shaft is released, and a third state in which said rotor shaft is locked against rotating and said pivot of said support means is in contact with said bearing; and said control means at least has a control mode for measuring the viscosity using the spring relaxation method, in which said elastic member is tightened up to a preset indicated value of said viscometer by operating said rotational driving means and said pivot protecting means is brought into said third state before a measurement starts, and at a start of the measurement said pivot protecting means is further brought into said second state to execute the measurement of the spring relaxation method.

2. The rotary viscometer according to claim 1, wherein; said control means controls said rotational driving means to execute the driving operation until said indicated value of said viscometer reaches said preset value during said control mode for measuring the viscosity using the spring relaxation method, providing said pivot protecting means is in third state before the start of the measurement.

3. The rotary viscometer according to claim 2, wherein said control means further has a control mode for carrying out a preparation process on the sample liquid before a series of operations which would be executed in said control mode for measuring the viscosity using the spring relaxation method when said control mode for measuring the viscosity using the spring relaxation method is selected, and in said control mode for carrying out a preparation process, executes control operations comprising, setting the pivot protecting means to said second state; rotating said rotor at a preset rotational speed for a preset period of time;

stopping the rotation of said rotor;

bringing the pivot protecting means into said third state; and leaving the sample liquid while maintaining the same state for a preset leave-period which can be set to an arbitrary value including a zero value.

4. The rotary viscometer according to claim 3, wherein said control means further has a control mode for studying a structural recovery of said sample liquid by repeating the measurement of the spring relaxation method including said preparation process, and executes control operation in said control mode so that operations executed during said preparation control mode and said control mode for measuring the viscosity using a spring relaxation method are repeated for a preset number of times.

5. The rotary viscometer according to claim 4, wherein said control means further has a control mode for a steady flow viscosity measurement in which the viscosity is measured while said rotor is rotated at a constant speed which is set to an arbitrary value, and, in said control mode for the steady flow viscosity measurement, executes control operations comprising, setting said pivot protecting means to said second state during the measurement state and then bringing into said first state after the measurement; and driving said second drive shaft by said rotational driving means during the measurement state.

6. The rotary viscometer according to claim 5, further comprising:

instruction accepting means for accepting instructions regarding a selection of said control mode and outputting a mode selecting signal in response to the accepted instruction; wherein said control means executes a control mode selected among said control mode for measuring the viscosity using the spring relaxation method, said control mode for studying the structural recovery of the sample liquid, and said control mode for the steady flow viscosity measurement, in response to said mode selecting signal.

7. The rotary viscometer according to claim 1, further comprising a first member secured at said rotor shaft, wherein said pivot protecting means comprises, a moving member attached to a portion of said viscometer, which stands still with respect to said rotor and is able to move up and down along a rotational axis of said rotor shaft which is unable to move in a circumferential direction of said rotational axis;

an actuator for driving said moving member up and down; wherein, said moving member has a second member for gearing with said first member and a third member for contacting with said first member to move said moving member and said first member together;

said pivot protecting means becomes said second state when said moving member is positioned at a lower limit of a movable range of said moving member;

said pivot protecting means becomes said third state in which said second member is geared with said first member to constrain the rotational motion of said second member and thus the rotation of said rotor shaft is locked when said moving member is reached at a predetermined position along said rotational axis, positioned above said lower limit;

said pivot protecting means becomes said first state in which said pivot and said bearing are separated while said third member pushes said rotor shaft via said first member upward when said moving member further moves upward from said predetermined position.

8. The rotary viscometer according to claim 7, further comprising:

detection means for detecting said moving member without having any physical contact, when said moving member has reached at said predetermined position along the rotational axis, at which said pivot protecting means becomes said third state.

9. A rotary viscometer which measures information regarding rheological properties of a liquid sample using a spring relaxation method, comprising a cone shaped rotor which is supported in such a way that said cone shaped rotor can move along its rotational axis and is driven to rotate while it contacts with the liquid sample to be measured;

rotational driving means having an elastic member, for driving said rotor to rotate via said elastic member;

locking means for realizing a second state in which said rotor is rotatably supported while an assumed peak top of the cone of said cone shaped rotor is in contact with a surface of a flat plate which holds the sample liquid with said cone shaped rotor, a first state in which said cone shaped rotor is moved along its rotational axis direction to separate from said flat plate and is locked therein against the rotation, and a third state in which said cone shaped rotor is locked while said assumed peak top of said cone shaped rotor is in contact with said flat plate;

indicated value detecting means for detecting an indicated value of said viscometer; and control means for controlling operations of said rotational driving means and said locking means, wherein said control means has a spring relaxation measurement control mode for measuring a viscosity using said spring relaxation method and a preparation control mode for executing a preparation process on the sample liquid before said spring relaxation measurement control mode starts a sequence of operations, and executes operations comprising, (a) in said spring relaxation measurement control mode, tightening said elastic member up to a preset state by operating said rotational driving means and setting said locking means to said third state, and bringing said locking means into said second state to start measurement operations using the spring relaxation method;

(b) in said preparation control mode, setting said locking means to said second state, rotating said cone shaped rotor at a preset rotational speed for a preset period of time, stopping said rotor, bringing said locking means into said third state, maintaining the same state in said locking means to leave the sample for a preset period of time which includes a zero value, and changing said control mode to said spring relaxation measurement control mode after an elapse of said preset period.

* * * * *

UNITED STATES PATENT AND TRADEMARK OFFICE
CERTIFICATE OF CORRECTION

PATENT NO. : 5,777,212

DATED : July 7, 1998

INVENTOR(S) : K. SEKIGUCHI et al.

It is certified that error appears in the above-identified patent and that said Letters Patent is hereby corrected as shown below:

In column 1, lines 28 and 41-42, "Theological" should be changed to --rheological--.

In column 2, line 49, "$10^{31\ 3}$/sec." should be changed to --$10^{-3}$/sec.--.

In column 2, line 60, "Theological" should be changed to --rheological--.

In column 3, lines 2, 7 and 36, "Theological" should be changed to --rheological--.

In column 4, line 59, "$(d\theta/dt_p$" should be changed to --$(d\theta/dt)_p$--.

In column 5, line 66, "$10^{31\ 3}$/sec." should be changed to --$10^{-3}$/sec.--.

In column 6, line 18, "$10^{31\ 3}$/sec." should be changed to --$10^{-3}$/sec.--.

In column 6, line 47, "Theological" should be changed to --rheological--.

In column 7, line 38, "for" should be changed to --to--.

In column 8, line 8, "Theological" should be changed to --rheological--.

In column 9, lines 18, 40 and 65, "Theological" should be changed to --rheological--.

In column 9, line 20, "steps of;" should be changed to --steps of--.

In column 9, lines 42 and 67, "comprising;" should be changed to --comprising--.

UNITED STATES PATENT AND TRADEMARK OFFICE
CERTIFICATE OF CORRECTION

PATENT NO. : 5,777,212
DATED : July 7, 1998
INVENTOR(S) : K. SEKIGUCHI et al.

It is certified that error appears in the above-identified patent and that said Letters Patent is hereby corrected as shown below:

In column 10, lines 15-16, there is no paragraph break.

In column 10, line 38, "tighten" should be changed to --tightened--.

In column 10, line 47, "measure" should be changed to --measures--.

In column 10, line 47, "Theological" should be changed to --rheological--.

In column 14, line 31, "Reserch" should be changed to --Research--.

In column 15, line 42, "steps of;" should be changed to --steps of--.

In column 16, line 39, "steps of;" should be changed to --steps of--.

In column 16, line 52, "comprises;" should be changed to --comprises--.

In column 17, line 26, "recovering" should be changed to --recovery--.

In column 17, line 29, "the," should be changed to --the--.

In column 18, line 47, "4c" should be changed to --4b--.

In column 31, line 19, "wherein;" should be changed to --wherein--.

In column 31, lines 36 and 62, "comprising," should be changed to --comprising:--.

UNITED STATES PATENT AND TRADEMARK OFFICE
CERTIFICATE OF CORRECTION

PATENT NO. : 5,777,212
DATED : July 7, 1998
INVENTOR(S) : K. SEKIGUCHI et al.

It is certified that error appears in the above-identified patent and that said Letters Patent is hereby corrected as shown below:

In column 32, line 6, "instruction;" should be changed to --instruction,--.

In column 32, line 16, "comprises," should be changed to --comprises--.

In column 32, line 54, "comprising" should be changed to --comprising:--.

In column 33, line 14, "comprising,&" should be changed to --comprising:--.

Signed and Sealed this

Eleventh Day of January, 2000

Attest:

Q. TODD DICKINSON

*Attesting Officer*   *Acting Commissioner of Patents and Trademarks*